(12) United States Patent
Xia et al.

(10) Patent No.: US 9,078,712 B2
(45) Date of Patent: Jul. 14, 2015

(54) PREFORMED DRUG-ELUTING DEVICE TO BE AFFIXED TO AN ANTERIOR SPINAL PLATE

(75) Inventors: Jusong Xia, Collierville, TN (US); Hai H. Trieu, Cordova, TN (US); William F. McKay, Memphis, TN (US); Newton H. Metcalf, Jr., Memphis, TN (US); Nikolas F. Kerr, Germantown, TN (US); Drew Amery, Jacksonville, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 880 days.

(21) Appl. No.: 12/610,020

(22) Filed: Oct. 30, 2009

(65) Prior Publication Data

US 2010/0266657 A1    Oct. 21, 2010

Related U.S. Application Data

(63) Continuation-in-part of application No. 12/409,089, filed on Apr. 15, 2009.

(51) Int. Cl.
| | |
|---|---|
| *A61K 9/00* | (2006.01) |
| *A61K 31/496* | (2006.01) |
| *A61K 31/65* | (2006.01) |
| *A61K 47/00* | (2006.01) |
| *A61B 17/80* | (2006.01) |
| *A61B 17/70* | (2006.01) |
| *A61K 47/24* | (2006.01) |
| *A61K 47/32* | (2006.01) |
| *A61K 47/34* | (2006.01) |
| *A61B 17/00* | (2006.01) |

(52) U.S. Cl.
CPC ......... *A61B 17/8042* (2013.01); *A61B 17/7059* (2013.01); *A61K 9/0024* (2013.01); *A61K 47/24* (2013.01); *A61K 47/32* (2013.01); *A61K 47/34* (2013.01); *A61B 2017/00004* (2013.01); *A61B 2017/00951* (2013.01)

(58) Field of Classification Search
USPC ....................................................... 424/423
See application file for complete search history.

(56) References Cited

U.S. PATENT DOCUMENTS

| | | |
|---|---|---|
| 4,006,741 A | 2/1977 | Arluck |
| 4,136,686 A | 1/1979 | Arluck |
| 4,286,586 A | 9/1981 | Potts |

(Continued)

FOREIGN PATENT DOCUMENTS

| | | |
|---|---|---|
| EP | 0393100 B1 | 10/1990 |
| WO | WO-8904682 A1 | 6/1989 |

OTHER PUBLICATIONS

Bayston, et al. "Antimicrobial activity of silicone rubber used in hydrocephalus shunts, after impregnation with antimicrobial substances", From the Department of Paediatrics, Children's Hospital, Sheffield, J Clin Pathol 198;134:1057-1062, Mar. 11, 1981.

(Continued)

*Primary Examiner* — Michael B Pallay
(74) *Attorney, Agent, or Firm* — Sorell Lenna & Schmidt LLP

(57) ABSTRACT

A drug-eluting device comprising a drug-eluting matrix containing at least one elutable drug, a method of manufacturing a preformed drug-eluting device, and an implant kit comprising the same.

20 Claims, 8 Drawing Sheets

(56) References Cited

U.S. PATENT DOCUMENTS

| | | |
|---|---|---|
| 4,369,769 A * | 1/1983 | Edwards ............... 606/257 |
| 4,917,686 A | 4/1990 | Bayston et al. |
| 5,061,281 A | 10/1991 | Mares et al. |
| 5,061,286 A | 10/1991 | Lyle |
| 5,217,493 A | 6/1993 | Raad et al. |
| 5,344,457 A | 9/1994 | Pilliar et al. |
| 5,458,653 A | 10/1995 | Davidson |
| 5,609,629 A | 3/1997 | Fearnot et al. |
| 5,624,704 A | 4/1997 | Darouiche et al. |
| 5,660,854 A | 8/1997 | Haynes et al. |
| 5,753,251 A | 5/1998 | Burrell et al. |
| 5,755,759 A | 5/1998 | Cogan |
| 5,820,607 A | 10/1998 | Tcholakian et al. |
| 5,824,049 A | 10/1998 | Ragheb et al. |
| 5,853,745 A | 12/1998 | Darouiche |
| 5,874,101 A | 2/1999 | Zhong et al. |
| 5,877,224 A | 3/1999 | Brocchini et al. |
| 5,879,697 A | 3/1999 | Ding et al. |
| 5,902,283 A | 5/1999 | Darouiche et al. |
| 5,951,558 A | 9/1999 | Fiz |
| 5,980,973 A | 11/1999 | Onyekaba et al. |
| 6,015,816 A | 1/2000 | Kostyniak et al. |
| 6,033,582 A | 3/2000 | Lee et al. |
| 6,042,875 A | 3/2000 | Ding et al. |
| 6,077,076 A | 6/2000 | Comfort |
| 6,096,070 A | 8/2000 | Ragheb et al. |
| 6,096,080 A | 8/2000 | Nicholson et al. |
| 6,153,212 A | 11/2000 | Mao et al. |
| 6,166,173 A | 12/2000 | Mao et al. |
| 6,228,393 B1 | 5/2001 | DiCosmo et al. |
| 6,238,687 B1 | 5/2001 | Mao et al. |
| 6,299,604 B1 | 10/2001 | Ragheb et al. |
| 6,322,797 B1 | 11/2001 | Mao et al. |
| RE37,479 E | 12/2001 | Kuslich |
| 6,335,029 B1 | 1/2002 | Kamath et al. |
| 6,428,579 B1 | 8/2002 | Valentini |
| 6,443,987 B1 | 9/2002 | Bryan |
| 6,478,822 B1 | 11/2002 | Leroux et al. |
| 6,527,801 B1 | 3/2003 | Dutta |
| 6,534,197 B2 | 3/2003 | Noda et al. |
| 6,558,686 B1 | 5/2003 | Darouiche |
| 6,558,734 B2 | 5/2003 | Koulik et al. |
| 6,559,119 B1 | 5/2003 | Burgess et al. |
| 6,582,715 B1 | 6/2003 | Barry et al. |
| 6,589,546 B2 | 7/2003 | Kamath et al. |
| 6,607,530 B1 | 8/2003 | Carl et al. |
| 6,652,525 B1 | 11/2003 | Assaker et al. |
| 6,692,498 B1 | 2/2004 | Niiranen et al. |
| 6,719,795 B1 | 4/2004 | Cornwall et al. |
| 6,730,064 B2 | 5/2004 | Ragheb et al. |
| 6,733,503 B2 | 5/2004 | Layrolle et al. |
| 6,736,815 B2 | 5/2004 | Ginn |
| 6,755,828 B2 | 6/2004 | Shevtsov et al. |
| 6,770,288 B2 | 8/2004 | Duirs |
| 6,770,729 B2 | 8/2004 | Van Antwerp |
| 6,774,278 B1 | 8/2004 | Ragheb et al. |
| 6,808,738 B2 | 10/2004 | DiCosmo et al. |
| 6,843,804 B2 | 1/2005 | Bryan |
| 6,843,807 B1 | 1/2005 | Boyce et al. |
| 6,899,713 B2 | 5/2005 | Shaolian et al. |
| 6,902,743 B1 | 6/2005 | Setterstrom et al. |
| 6,916,310 B2 | 7/2005 | Sommerich |
| 6,919,100 B2 | 7/2005 | Narayanan |
| 6,921,811 B2 | 7/2005 | Zamora et al. |
| 6,923,811 B1 | 8/2005 | Carl et al. |
| 6,951,561 B2 | 10/2005 | Warren et al. |
| 6,964,667 B2 | 11/2005 | Shaolian et al. |
| 6,986,771 B2 | 1/2006 | Paul et al. |
| 6,989,011 B2 | 1/2006 | Paul et al. |
| 6,991,802 B1 | 1/2006 | Ahola et al. |
| 6,994,883 B2 | 2/2006 | Layrolle et al. |
| 6,998,134 B2 | 2/2006 | Schmidmaier et al. |
| 7,052,497 B2 | 5/2006 | Sherman et al. |
| 7,056,533 B2 | 6/2006 | Chudzik et al. |
| 7,056,550 B2 | 6/2006 | Davila et al. |
| 7,077,859 B2 | 7/2006 | Sirhan et al. |
| 7,090,668 B1 | 8/2006 | U et al. |
| 7,101,840 B2 | 9/2006 | Brocchini et al. |
| 7,105,018 B1 | 9/2006 | Yip et al. |
| 7,105,023 B2 | 9/2006 | Eckman |
| 7,144,422 B1 | 12/2006 | Rao |
| 7,157,096 B2 | 1/2007 | Zhang et al. |
| 7,163,561 B2 | 1/2007 | Michelson |
| 7,169,404 B2 | 1/2007 | Hossainy et al. |
| 7,175,611 B2 | 2/2007 | Mitchnick |
| 7,182,783 B2 | 2/2007 | Trieu |
| 7,189,409 B2 | 3/2007 | Pirhonen et al. |
| 7,192,445 B2 | 3/2007 | Ellingsen et al. |
| 7,192,604 B2 | 3/2007 | Brown et al. |
| 7,238,203 B2 | 7/2007 | Bagga et al. |
| 7,238,363 B2 | 7/2007 | Mansouri et al. |
| 7,279,175 B2 | 10/2007 | Chen et al. |
| 7,303,814 B2 | 12/2007 | Lamberti |
| 7,309,338 B2 | 12/2007 | Cragg |
| 7,314,857 B2 | 1/2008 | Madhyastha |
| 7,320,798 B2 | 1/2008 | Zhang et al. |
| 7,320,799 B2 | 1/2008 | Zhang et al. |
| 7,335,205 B2 | 2/2008 | Aeschlimann et al. |
| 7,378,106 B2 | 5/2008 | Hossainy et al. |
| 7,410,502 B2 | 8/2008 | Ellingsen et al. |
| 7,410,665 B2 | 8/2008 | Ragheb et al. |
| 7,413,574 B2 | 8/2008 | Yip et al. |
| 7,413,806 B2 | 8/2008 | Ong et al. |
| 7,416,558 B2 | 8/2008 | Yip et al. |
| 7,431,734 B2 | 10/2008 | Danoff et al. |
| 7,445,628 B2 | 11/2008 | Ragheb et al. |
| 7,470,283 B2 | 12/2008 | Dutta |
| 2002/0090398 A1 | 7/2002 | Dunn et al. |
| 2002/0147496 A1 | 10/2002 | Belef et al. |
| 2002/0147497 A1 | 10/2002 | Belef et al. |
| 2002/0188037 A1 | 12/2002 | Chudzik et al. |
| 2003/0039689 A1 | 2/2003 | Chen et al. |
| 2003/0045937 A1 | 3/2003 | Ginn |
| 2003/0099762 A1 | 5/2003 | Zhang et al. |
| 2003/0125739 A1 | 7/2003 | Bagga et al. |
| 2003/0139814 A1 | 7/2003 | Bryan |
| 2003/0229319 A1 | 12/2003 | Mitchnick |
| 2004/0030342 A1 | 2/2004 | Trieu et al. |
| 2004/0043052 A1 | 3/2004 | Hunter et al. |
| 2004/0047909 A1 | 3/2004 | Ragheb et al. |
| 2004/0059333 A1 | 3/2004 | Carl et al. |
| 2004/0083002 A1 | 4/2004 | Belef et al. |
| 2004/0127906 A1 | 7/2004 | Culbert et al. |
| 2004/0158246 A1 | 8/2004 | Assaker et al. |
| 2004/0158248 A1 | 8/2004 | Ginn |
| 2004/0172132 A1 | 9/2004 | Ginn |
| 2004/0220571 A1 | 11/2004 | Assaker et al. |
| 2004/0236327 A1 | 11/2004 | Paul et al. |
| 2004/0236328 A1 | 11/2004 | Paul et al. |
| 2005/0019404 A1 | 1/2005 | Sung et al. |
| 2005/0027360 A1 | 2/2005 | Webb et al. |
| 2005/0031666 A1 | 2/2005 | Trieu |
| 2005/0033289 A1 | 2/2005 | Warren et al. |
| 2005/0079199 A1 | 4/2005 | Heruth et al. |
| 2005/0079200 A1 | 4/2005 | Rathenow et al. |
| 2005/0220837 A1 | 10/2005 | Disegi et al. |
| 2005/0240076 A1 | 10/2005 | Neisz et al. |
| 2005/0244459 A1 | 11/2005 | DeWitt et al. |
| 2005/0255142 A1 | 11/2005 | Chudzik et al. |
| 2005/0271694 A1 | 12/2005 | Mansouri et al. |
| 2005/0276841 A1 | 12/2005 | Davis et al. |
| 2006/0015105 A1 | 1/2006 | Warren et al. |
| 2006/0034891 A1 | 2/2006 | Lawin et al. |
| 2006/0039946 A1 | 2/2006 | Heruth et al. |
| 2006/0041259 A1 | 2/2006 | Paul et al. |
| 2006/0047341 A1 | 3/2006 | Trieu |
| 2006/0051392 A1 | 3/2006 | Heruth et al. |
| 2006/0057277 A1 | 3/2006 | Chappa |
| 2006/0089722 A1 | 4/2006 | Montevecchi et al. |
| 2006/0093646 A1 | 5/2006 | Cima et al. |
| 2006/0115457 A1 | 6/2006 | Hnojewyj |
| 2006/0121083 A1 | 6/2006 | Mor |
| 2006/0127438 A1 | 6/2006 | Hunter et al. |
| 2006/0198903 A1 | 9/2006 | Storey et al. |

(56) References Cited

U.S. PATENT DOCUMENTS

| | | |
|---|---|---|
| 2006/0204537 A1 | 9/2006 | Ratner et al. |
| 2006/0229615 A1 | 10/2006 | Abdou |
| 2006/0235530 A1 | 10/2006 | Shelokov |
| 2007/0016163 A1* | 1/2007 | Santini et al. ............... 604/500 |
| 2007/0050010 A1 | 3/2007 | Bates et al. |
| 2007/0071789 A1 | 3/2007 | Panteildis et al. |
| 2007/0104758 A1 | 5/2007 | Hamilton et al. |
| 2007/0116734 A1 | 5/2007 | Akash |
| 2007/0118132 A1 | 5/2007 | Culbert et al. |
| 2007/0123868 A1 | 5/2007 | Cullbert et al. |
| 2007/0125247 A1 | 6/2007 | Kunstmann et al. |
| 2007/0134287 A1 | 6/2007 | Troxel et al. |
| 2007/0141100 A1 | 6/2007 | Sung |
| 2007/0154621 A1 | 7/2007 | Raad |
| 2007/0168012 A1 | 7/2007 | Ragheb et al. |
| 2007/0198040 A1 | 8/2007 | Buevich et al. |
| 2007/0212387 A1 | 9/2007 | Patravale et al. |
| 2007/0218102 A1 | 9/2007 | Chudzik et al. |
| 2007/0224162 A1 | 9/2007 | Roby et al. |
| 2007/0224243 A1* | 9/2007 | Bayston ............... 424/423 |
| 2007/0265622 A1 | 11/2007 | Aeschlimann et al. |
| 2007/0270812 A1* | 11/2007 | Peckham ............... 606/61 |
| 2007/0270858 A1 | 11/2007 | Trieu et al. |
| 2007/0287129 A1 | 12/2007 | Ihde |
| 2007/0293948 A1 | 12/2007 | Bagga et al. |
| 2007/0299520 A1 | 12/2007 | Trieu et al. |
| 2007/0299535 A1 | 12/2007 | Ihde |
| 2008/0008988 A1 | 1/2008 | McKay et al. |
| 2008/0015578 A1 | 1/2008 | Erickson et al. |
| 2008/0038316 A1 | 2/2008 | Wong |
| 2008/0045961 A1 | 2/2008 | Aeschlimann et al. |
| 2008/0063693 A1 | 3/2008 | Cook et al. |
| 2008/0089952 A1 | 4/2008 | Hunter et al. |
| 2008/0107711 A1 | 5/2008 | Shelokov |
| 2008/0108824 A1 | 5/2008 | Isch et al. |
| 2008/0113000 A1 | 5/2008 | Hunter et al. |
| 2008/0128315 A1 | 6/2008 | Buevich et al. |
| 2008/0132992 A1 | 6/2008 | Bates et al. |
| 2008/0145514 A1 | 6/2008 | Hunter et al. |
| 2008/0152784 A1 | 6/2008 | Stenzel |
| 2008/0154311 A1 | 6/2008 | Staeubli |
| 2008/0154368 A1 | 6/2008 | Justis et al. |
| 2008/0154373 A1 | 6/2008 | Protopsaltis et al. |
| 2008/0161907 A1 | 7/2008 | Chen et al. |
| 2008/0183152 A1 | 7/2008 | Raad et al. |
| 2008/0220041 A1 | 9/2008 | Brito et al. |
| 2008/0221623 A1 | 9/2008 | Gooch |
| 2008/0221624 A1 | 9/2008 | Gooch |
| 2008/0241212 A1 | 10/2008 | Moses et al. |
| 2008/0241217 A1 | 10/2008 | Hunter et al. |
| 2008/0269742 A1 | 10/2008 | Levy et al. |
| 2008/0269810 A1 | 10/2008 | Zhang et al. |
| 2008/0299202 A1 | 12/2008 | Marenzi et al. |
| 2009/0018559 A1 | 1/2009 | Buevich et al. |
| 2009/0088548 A1 | 4/2009 | Moses et al. |

OTHER PUBLICATIONS

Rushton, Implant infections and antibiotic-impregnated silicone rubber coating, Journal of Neurology, Neurosurgery, and Psychiatry 1989;52:223-229, London, UK.

* cited by examiner

PREFORMED DRUG-ELUTING DEVICE TO BE AFFIXED TO AN ANTERIOR SPINAL PLATE

CROSS-REFERENCE TO RELATED APPLICATIONS

This application is a continuation-in-part of U.S. patent application Ser. No. 12/409,089, filed Mar. 23, 2009, the entirety of which is incorporated by reference.

BACKGROUND OF THE INVENTION

This invention relates generally to plates possessing drug-eluting or drug-diffusing capability. More particularly, the invention is for an anterior spinal plate having such capacity.

Numerous orthopedic implants, including spinal implants such as anterior spinal plates, are known to possess adherent coatings, layers or films containing one or more drugs, e.g., medicaments, therapeutics, biologicals or other bioactive substances, etc., such as antimicrobials, antibacterials, antibiotics, antifungicides, anti-inflammatories, and the like. Following the installation of such an implant in the body, the drug(s) present in the coating elutes therefrom over time into the region of surrounding tissue to achieve the desired drug action(s).

One of the problems encountered in the manufacture of an orthopedic implant possessing a drug-eluting coating involves the sterilization of such a device. The more economical methods of sterilization utilize steam under pressure, e.g., as produced in an autoclave. While such sterilization methods are known to be highly effective, they are subject to a major disadvantage where thermally sensitive drugs are concerned and therefore are of limited use. While the conventional use of sterilizing radiation or a sterilant gas such as ethylene oxide can reduce the risk of damaging or partially to completely inactivating the drug component(s) present in the coating component of an orthopedic implant, such sterilization methods are relatively expensive. While it is possible in principle to apply a drug-containing coating to a pre-sterilized implant under sterile conditions followed by the sterile packaging of the coated implant, such an approach to providing a packaged sterile orthopedic implant, which avoids subjecting the drug(s) contained in its drug-eluting coating to thermal decomposition or deactivation, is largely an impractical one.

Therefore, what is needed is a drug-eluting device that can be applied to an orthopedic implant in vivo or in vitro where the drug-eluting device can be sterilized separately from the implant and configured to fit a variety of such implants. The present invention provides such a device and is described in further detail below.

SUMMARY OF THE INVENTION

In accordance with the present invention, there is provided a drug-eluting device comprising a drug-eluting biocompatible matrix containing at least one elutable drug and at least one substance that facilitates non-irritating motion of the device across adjacent tissue, said device configured to fit an anterior spinal plate and comprises at least one affixation feature for providing a method of attaching the device to said anterior spinal plate. Useful drug-eluting biocompatible matrices include hydrogels, and polymers such as poly(L-lactic acid), poly(glycolic acid), poly(lactide-co-glycolide), polydioxanone, polyorthoesters, polyanhydrides, thermoset resins, such as polyurethane foam, or an elastomer such as polyurethane or silicone and the like. For example, such polymers include but are not limited to a polyvinyl alcohol, a polyacrylic acid, a polyarylamide, a poly(acrylonitrile-acrylic acid), a polyurethane, a polyethylene glycol, a poly(N-vinyl-2-pyrrolidone), a gelatin, a collagen, a polysaccharide, a cellulose, silicone and combinations thereof.

The present invention can also be made from hydrogels or silicone impregnated with antibacterial/antimicrobial agents. The present invention can also be made from hydrogels or silicone impregnated with antibacterial/antimicrobial agents such as clindamycin, minocycline and/or rifampin. The present invention can also be made from matrix materials, such as silicone, impregnated with antibacterial/antimicrobial agents such as clindamycin, e.g., at weight percent of between about 0.02% and about 0.3%, between about 0.09% and about 0.3%, between about 0.1% and about 0.2% or about 0.15% and rifampin, e.g., at weight percent of between about 0.01% and about 0.1%, between about 0.04% and about 0.07%, between about 0.05% and about 0.06%, or about 0.054%. The present invention can also be made from matrix materials, such as silicone, impregnated with antibacterial/antimicrobial agents such as minocyclin, e.g., at weight percent of between about 0.02% and about 0.8%, between about 0.09% and about 0.3%, between about 0.1% and about 0.2% or about 0.2% and rifampin, e.g., at weight percent of between about 0.03% and about 1.0%, between about 0.09% and about 0.5%, between about 0.1% and about 0.4%, or about 0.3%. Hyrdogels or matrix materials may be hydrated or unhydrated.

When an unhydrated hydrogel is employed, it may be hydrated either just prior to implantation using a sterile solution, or after implantation using in vivo fluids. Once hydrated, a hydrogel will have increased in volume.

Hydrogels that can be used for the present invention may also be made non-bioresorbable by means of the process in which they are produced as well as the molecular composition. Various degrees of bioresorbablity can also be accomplished by varying the amount of cross-linking in the hydrogel.

In accordance with the present invention, there is provided a method of manufacturing a preformed drug-eluting device comprising forming a drug-eluting biocompatible matrix from a silicone elastomeric material into an hollow cylindrical shape having a top end, a bottom end and a wall extending between the top end and the bottom end, wherein the wall has an interior face and an exterior face; optionally creating an incision along the length of the wall from the top end to the bottom end to produce a drug-eluting vehicle; creating a solution comprising a protein synthesis inhibition antibiotic and an RNA polymerase inhibitor antibiotic, wherein the solution optionally comprises methylene chloride, xylene, and/or chloroform; optionally, the drug solution concentration is between about 0.1 to about 0.8 grams of each antibiotic per deciliter of solution; immersing the drug-eluting vehicle in the solution for a period of time, for example, between 30 minutes and an hour; removing the drug-eluting vehicle from the solution; optionally the method may include purging the drug-eluting vehicle with nitrogen; and drying the drug-eluting vehicle under a vacuum to produce a preformed drug-eluting device. Optionally, the method may further include packaging the drug-eluting device and/or sterilizing the drug-eluting device in a chamber heated with steam, e.g., by autoclaving the drug-eluting device.

In accordance with the present invention, there is provided a preformed drug-eluding device wherein clindamycin is present in the drug-eluting biocompatible matrix as about 0.15 wt % of the matrix and rifampin is present in the drug-eluting biocompatible matrix as about 0.05 wt % of the matrix.

In accordance with the present invention, there is provided a preformed drug-eluding device wherein rifampin is present in the drug-eluting biocompatible matrix as about 0.3 wt % of the matrix and minocycline is present in the drug-eluting biocompatible matrix as about 0.2 wt % of the matrix.

In accordance with the present invention, there is provided a preformed drug-eluding device wherein the thickness of the drug-eluting device is between about 0.1 mm to about 7 mm, between about 0.2 mm to about 4 mm, between about 0.1 mm to about 2.5 mm, between about 0.1 mm to about 2 mm, between about 0.1 mm to about 1 mm, or between about 0.3 mm to about 1 mm.

According to a further aspect of the present invention, there is provided an implant kit comprising an anterior spinal plate and at least one preformed drug-eluting device. According to another exemplary embodiment, the invention provides an implant kit comprising at least one preformed drug-eluting device in a packaging, wherein the at least one preformed drug-eluting device has been sterilized inside the packaging. According to yet another exemplary embodiment, the invention provides an implant kit comprising at least one sterilized preformed drug-eluting device in a packaging, wherein the at least one preformed drug-eluting device is configured to mate with a predetermined implant and cover soft tissue exposed surfaces thereon, thereby delivering the antimicrobial drugs to the soft tissue area and also reducing mechanical irritation during motion by the patient.

The distinction between a drug-eluting coating as utilized by heretofore known orthopedic implants and the preformed drug-eluting device of this invention is a fundamental one and is of considerable significance for addressing the sterilization problem discussed herein. Thus, an orthopedic implant, e.g., an anterior plate, according to the present invention can be supplied to an orthopedic surgeon as two separately sterilized components, one being the implant which has been sterilized by the economical autoclave method and the other being a preformed drug-eluting device which has been sterilized separately, optionally by some other method, e.g., the use of sterilizing radiation or sterilant gas, that does not subject the drug(s) present therein to any significant level of decomposition, denaturation or deactivation. The surgeon then has the choice of affixing the drug-eluting device to the implant just prior to, during or just after installation of the implant in the body as the particular circumstances may require.

Another major advantage of the drug-eluting device of the invention is that it can be combined with an anterior spinal plate at the time of surgery to form a specific implant device and a specific drug-eluting device combination, wherein each anterior spinal plate can be paired with multiple drug-eluting devices, each differing in the nature and/or amounts of the drug(s) contained therein and/or the nature of the drug-eluting composition, or drug-eluting material, from which the device is fabricated thereby offering the surgeon considerable flexibility for choosing the optimal anterior spinal plate and the optimal preformed drug-eluting device for affixation thereto for a particular patient's circumstances and needs. It is far more practical to provide such flexibility of choice in the case of an in situ assembled drug-eluting anterior spinal plate as in the present invention than to provide the same number of choices for a pre-coated implant of the prior art.

To illustrate this advantage, consider the case where a surgeon desires to choose from among 5 different sizes, designs or configurations of anterior spinal plate and five different drugs (and drug combinations) to be eluted. In the case of the in situ assembled anterior spinal plate of the invention, the surgeon need only have on hand 5 choices of anterior plates and 5 choices of pre-formed drug-eluting devices to meet all contemplated situations totaling 25 different combinations of assembly of the 5 different anterior spinal plates of the present invention with the 5 different drug-eluting devices. However, it would require 25 pre-coated anterior spinal plates of the prior art to provide the same total number of choices. This scenario points to yet another advantage of the invention over the prior art, namely, it presents the surgeon with the opportunity to choose from among all suppliers' anterior spinal plates to which a preformed drug-eluting device may be affixed. The surgeon is therefore not limited to the anterior spinal plate offerings of just one or a few suppliers but has as many choices in this regard as the then-current commercial situation makes available.

BRIEF DESCRIPTION OF THE DRAWINGS

FIG. 9a shows a rabbit suture 7 days after implant of a control tissue which shows clear signs of infection. The site of infection is circled and labeled in FIG. 9a.

DETAILED DESCRIPTION OF THE INVENTION

Figure 1:
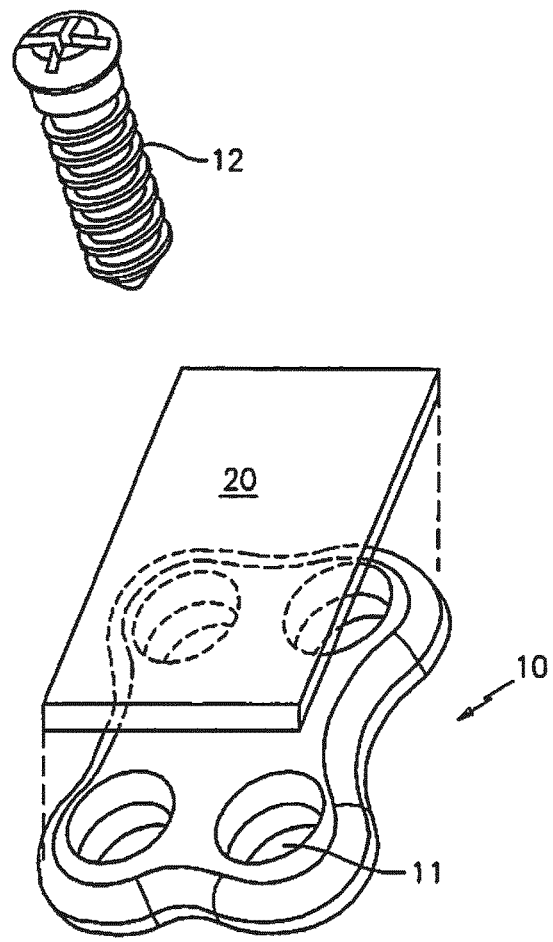
FIG. 1 is a perspective view of one embodiment of an anterior spinal plate and a preformed drug-eluting device of this invention about to be affixed to the plate.

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems, or devices, and any further applications of the principles of the invention as described herein, are contemplated as would normally occur to one skilled in the art to which the invention relates.

The term "about" shall be understood herein to mean less than or equal to a 15% deviation from the recited value, for example, a rifampin concentration of about 0.054 wt % means rifampin at 0.054 wt %±15% (or, rounding to the same decimal place, between 0.053 wt % and 0.055 wt %).

The term "anterior spinal plate" shall be understood herein to include the means, e.g., screws or other fasteners, by which the plate is secured to spinal bone.

The term "preformed" as it is applied to the drug-eluting device of the invention is to be understood as distinguishing the drug-eluting device from a drug-eluting coating which is manufactured upon a surface of the implant. Thus, the drug-eluting device affixed to the anterior spinal plate of the invention, in contrast to known orthopedic implants possessing a drug-eluting coating, film, or layer manufactured thereon, is not produced upon a surface of the implant but upon some other surface if, indeed, it is produced upon a surface of any substrate at all. It is only after the fabrication of the drug-eluting device of the invention that the device will be affixed to the anterior spinal plate.

The term "biocompatible" as applied to the drug-eluting material from which the drug-eluting device herein is fabricated shall be understood in its ordinary art-recognized sense as describing a material exhibiting a relatively low chronic tissue response for the period that the material is present in the body of a subject into which the drug-eluting device has been implanted.

The expression "drug-eluting" shall be understood to refer to any and all mechanisms, e.g., diffusion, migration, permeation and/or desorption, by which the drug(s) incorporated in the drug-eluting material pass therefrom over time into the surrounding body tissue.

The expression "drug-eluting material" shall be understood herein to mean any natural, synthetic or semi-synthetic material capable of acquiring and retaining a desired shape or configuration and into which one or more drugs can be incorporated and from which the incorporated drug(s) are capable of eluting over time.

The expression "elutable drug" shall be understood to mean any drug or combination of drugs having the ability to pass over time from the drug-eluting matrix in which it is incorporated into the surrounding areas of the body.

The term "drug" includes all medically useful bio-affecting and body-treating compositions.

The term "weight percent" or "wt %" means the ratio of the drug weight to the weight of the biocompatible matrix, e.g., the silicone after sterilization, for example, an initial concentration of rifampin of about 0.0738 wt % with about a 30 minute autoclave time will result in a final wt % of about 0.054 in the sterilized product.

Other than where otherwise indicated, all numbers expressing amounts of materials, concentrations, quantified properties of materials, and so forth, stated in the specification and claims are to be understood as being modified in all instances by the term "about" or "approximately."

It will also be understood that any numerical range recited herein is intended to include all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Anterior spinal plates of many configurations, sizes and functions and their use in the surgical treatment of bone injuries and defects are well known in the art. The plates can be fabricated from a wide range of materials including metals, synthetic polymers, ceramics and bone. Examples of these materials include metals such as medical grade stainless steel, titanium and titanium alloys, and the like, synthetic polymers such as thermoplastic polymers, thermoset polymers, elastomers, and the like, ceramics such as pyrolytic carbon, carbon fibers, and their composites, zirconia, alumina, titanic and their composites, and the like, bone, e.g., autograft, allograft, xenograft or transgenic cortical and/or corticocancellous bone obtained, e.g., from the femur, tibia, fibula radius and/or ulna and provided as a single unit or as a composite built up from smaller bone elements and/or bone-derived particles.

An anterior spinal plate, can come in many different sizes and configurations for installation at various cervical, thoracic and lumbar regions of the spine. Its fastener components (typically screws) aside, an anterior spinal plate can be provided as a single unit or as an assemblage of two or more sub-units. Illustrative spinal plates are those described in, among others, U.S. Pat. Nos. 6,193,721; 6,206,882; 6,224,602; 6,228,085; 6,258,089; 6,342,055; 6,413,259; 6,533,786; 6,602,255; 6,602,256; 6,605,090; 6,613,053; 6,679,883; 6,755,833; 6,761,719; 7,041,105; 7,169,150; 7,186,256; 7,306,605; 7,468,069; and 7,481,829, and U.S. Patent Application Publications Nos. 2004/0204712; 2005/0192577; 2005/0228386; 2007/0043369; 2007/0233110; 2007/0276371; 2008/0234753; 2009/0012571; and 2009/0024171, the entire contents of which are incorporated by reference herein.

Coating-containing drug reservoirs that are distinguishable from the present invention have been described in U.S. Patent Application Publication Nos. 2005/0031666; 2007/0299520; 2006/0047341; 2007/0270858; 2004/0030342; and 2007/0173934, the entire contents of which are incorporated by reference herein.

Prior to, during or following the surgical installation of a selected anterior spinal plate, there is affixed to at least a portion of the surface of the plate, e.g., a portion of an exposed surface, at least one preformed drug-eluting device fabricated from a drug-eluting matrix and containing one or more elutable drugs in accordance with this invention.

The drug-eluting device and/or drug-eluting matrix can possess a generally planar shape, e.g., that of a square, rectangle, circle, oval, etc., or a more complex, three-dimensional shape which is identical to or approximates that of the surface of the anterior spinal plate to which it is to be affixed. The drug-eluting matrix can be formed from a material of homogeneous or heterogeneous composition, can possess a single layer or multiple layers (i.e., a laminate), can be rigid, flexible or semiflexible, can be stretchable (elastic) or heat shrinkable so as to engagedly fit some portion of its associated plate, or essentially nonstretchable (inelastic), can be porous or nonporous, can vary considerably in its average dimensions, etc.

In one embodiment of the present invention, the drug-eluting matrix and/or drug-eluting device is in the form of a planer sheet having at least one extension configured to fit within a complimentary cavity located on the surgical plate. The planer sheet having the drug-eluting matrix can be positioned so that the extension (or extensions) snap (or pressure fit) into and/or onto the anterior spinal plate. The planer sheet may be of any geometric size or shape. In this embodiment, the surface of the drug eluting matrix is in direct contact with at least one surface of the plate. Unlike those embodiments that use an adhesive to affix the matrix to the plate, in this configuration, the drug is eluted from the drug-eluting matrix towards the plate as well as to the surrounding soft tissue. In other words, in this embodiment the drug passes directly to the surface of the plate so as to prevent any infections that may arise between the drug eluting layer and the surface of the plate. Since no contact between surfaces is absolutely perfect, gaps and/or air pockets can and will arise between the drug-eluting matrix and the surface of the plate. These gaps and/or pockets can develop infections which can be prevented by use of antimicrobial/anti-infectious compounds which elute from the matrix into the pockets that may form. In addition to preventing infection in these gaps/pockets, the drug-eluting matrix also elutes into the soft tissue surrounding the plate.

Figure 5:
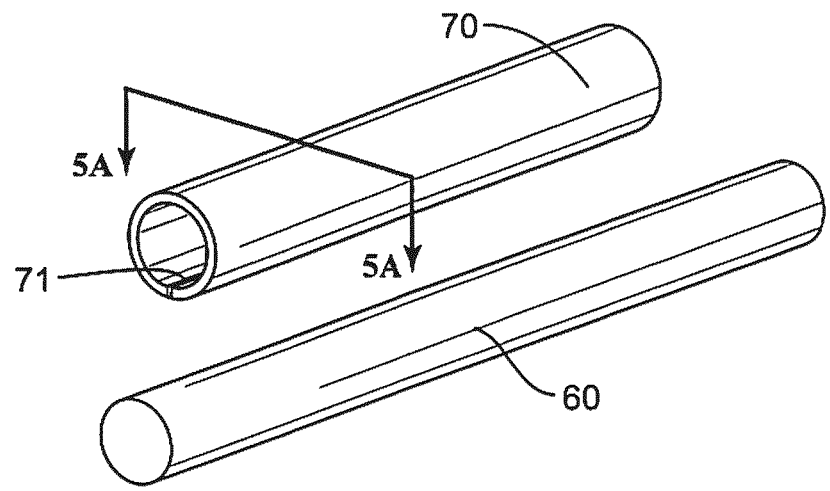
FIG. 5 is a perspective view of the rod component of a spinal fixation system and a performed drug-eluting sleeve in accordance with this invention about to be affixed to the rod.

In another embodiment of this invention, the drug-eluting device is provided as a cylinder or sleeve dimensioned to achieve a tight fit about the rod component of a spinal fixation system. The cylinder or sleeve can be fabricated from a heat-shrinkable polymer and be slightly oversized to facilitate its being slipped over the rod prior to its installation in the body. Application of a suitable level of heat, even body heat, which does not negatively affect the drug component(s) of the sleeve to any significant extent will cause the sleeve to firmly affix itself to the rod. Alternatively, the cylinder or sleeve can be provided with a lengthwise slot allowing it to be press-fitted to the rod before, during or after its installation in the body as illustrated in FIG. 5.

In yet another embodiment of the invention, the anterior spinal plate can be configured to possess at least one locking element that allows the drug-eluting matrix of the present invention to be affixed thereto. The locking element is configured so as to allow fixed engagement of the drug-eluting device. This type of fixed engagement directly attaches the drug-eluting device immediately adjacent to the surface of the plate. Other variations and configurations of this locking element/drug-eluting device embodiment can include detent locking mating configurations, friction fit, pressure fit and various other configurations known in the art.

The drug-eluting device can be dimensioned and configured as desired by any suitable technique, e.g., molding, machining, die-cutting from a larger sheet or section, etc., and can be dimensioned and configured by the surgeon or assistant personnel, e.g., by scissors if the nature of the drug-eluting matrix and/or drug-eluting device permits, at or near the time the drug-eluting device is to be affixed to the selected anterior spinal plate.

The drug-eluting matrix component of the drug-eluting device can be fabricated from amongst any of the numerous biocompatible materials heretofore known for providing drug-eluting devices. Useful matrices include non-bioresorbable, or non-bioabsorbable, materials and bioresorbable, or bioabsorble, materials. Natural, semi-synthetic and fully synthetic polymers of both types are well known in the art for use as drug-eluting matrices.

Among the useful non-bioresorbable drug-eluting matrices are biocompatible polymers such as polyurethanes, silicones (polysiloxanes), polyesters, polyamides, polyolefins such as polyethylene, polypropylene, polyisobutylene and their copolymers, acrylic polymers and copolymers, vinyl halide polymers and copolymers, fluorocarbon polymers such as polytetra fluoroethylene, polyvinyl ethers, polyacrylonitriles, polyvinyl ketones, polyvinyl aromatics such as polystyrene, polyvinyl esters, polycarbonates, polyimides, polyethers, epoxy resins, compatible blends of these and other biocompatible polymers, and the like.

Useful bioresorbable drug-eluting matrices include hydrogels, poly(L-lactic acid), poly(glycolic acid), poly(lactide-co-glycolide), polydioxanone, polyorthoesters, polyanhydrides, and the like.

If desired, the drug-eluting device herein can be provided as a laminate with, e.g., a first layer (the layer closest to the surface of the anterior spinal plate to which the device will be affixed) fabricated from a non-bioresorbable matrix containing one or more elutable drugs and superimposed thereon a second layer of bioresorbable matrix containing the same or different drug(s) as the first layer.

The drug-eluting properties of a drug-eluting matrix, principally the rate of release of its drug component(s) into the surrounding body tissues, is of prime importance. Those skilled in the art employing known procedures can readily select the optimum drug-eluting matrix material for a particular drug or drug combination and drug loading(s).

The selected drug(s) may be incorporated in the drug-eluting matrix during and/or after the formation of the drug-eluting matrix material. The incorporation of drug can be substantially uniform or, optionally, the drug(s) can be distributed in the drug-eluting matrix in gradient fashion or in distinct zones of concentration employing any of several methods known in the art. Thus, e.g., a greater concentration of drug(s) at or near the exposed surface of the drug-eluting matrix can be made to provide an initially higher concentration of drug(s) in the surrounding tissues followed by a reduction in delivered drug concentration (and perhaps longer term drug delivery as well if desired) as the more interior regions or zones of lower drug concentration within the drug-eluting matrix begin eluting the drug. This gradient or zonal distribution of drug in the drug-eluting matrix can be utilized to initially deliver a higher concentration of one drug in a drug combination followed by later delivery of a higher concentration of another drug in the drug combination.

Useful drug incorporation procedures include combining the selected elutable drug(s) with the precursor(s) of the matrix and thereafter forming the matrix. Thus, in the case of a polymeric matrix, e.g., an open cell polyurethane foam, the drug(s) can be admixed with the precursor reactants (e.g., polyisocyanate and polyol among other components of the polyurethane foam-forming reaction mixture) with the resulting polyurethane foam entraining the drug(s).

Another drug incorporation procedure involves contacting the drug-eluting matrix material with a drug-containing solvent medium which dissolves the matrix and, following evaporation of the solvent(s), leaves the drug(s) in the reconstituted matrix. A similar procedure involves contacting the drug-eluting matrix with a drug-containing swelling agent or solvent and allowing the drug(s) to diffuse into the matrix and then removing the swelling agent or solvent.

When an open cell matrix is used as the drug-eluting vehicle, e.g., the aforementioned polyurethane foam or a silicone elastomer, the desired drug(s) can be incorporated in the matrix by immersion in a suitable aqueous and/or organic solvent solution of the drug(s) followed by draining excess solvent and if desired, drying.

The drug-eluting matrix can also be fashioned from organic and/or inorganic particulate material and drug bonded together in the desired configuration employing a biocompatible bonding or binder material. Examples of a binder material include the resorbable or non-resorbable biomaterials mentioned above. Additional examples of binder materials include those used in the pharmaceutical industry such as polysaccharides, celluloses, collagen material, gelatin material, synthetic bioresorbable polymer, etc.

These and/or other known techniques can also be used to incorporate one or more non-drug materials in the matrix component of the drug-eluting device herein. Among some optional non-drug materials that can be incorporated in the drug-eluting matrix are diluents, carriers, excipients, stabilizers, permeation enhancers, surface active agents, and the like, in known and conventional amounts.

The amounts of elutable drug for incorporation in the drug-eluting matrix herein will depend on a number of factors well understood by those skilled in the art including the nature of the selected drug(s), the nature, amounts and configuration of the selected matrix and the desired profile (rate and duration) of drug release into the surrounding tissues. Again, empirical investigation employing known and conventional procedures can be utilized by those skilled in the art to arrive at an optimum concentration of specific drug(s) for a specific matrix arrangement. The concentration of drug(s) and the drug-eluting profile of the matrix component of the drug-eluting device will be such as to deliver a therapeutically effective concentration of the desired drug(s) for a therapeutically useful duration. Total concentration of deliverable drug can range, e.g., from 0.03 wt % to 2 wt %, from 0.03 wt % to 0.5 wt %, or from 0.03 wt % to 0.3 wt % of the drug-eluting matrix and can provide eluted drug(s) in therapeutically useful amounts for periods ranging e.g., for at least 24 hours and preferably at least 70, 100, 250, 500 or even 750 hours or more. In certain embodiments, the duration of effective drug release can range from 2 days to 3 weeks. The present invention can also be made from a biocompatible matrix, such as silicone, impregnated with antibacterial/antimicrobial agents such as clindamycin, e.g., at weight percent of between about 0.02% and about 0.3%, between about 0.09% and about 0.3%, between about 0.1% and about 0.2% or about 0.15% and rifampin, e.g., at weight percent of between about 0.01% and about 0.1%, between about 0.04% and about 0.07%, between about 0.05% and about 0.06%, or about 0.054%. The present invention can also be made from hydrogels impregnated with antibacterial/antimicrobial agents such as minocyclin, e.g., at weight percent of between about 0.02% and about 0.8%, between about 0.09% and about 0.3%, between about 0.1% and about 0.2% or about 0.2% and rifampin, e.g., at weight percent of between about 0.03% and about 1.0%, between about 0.09% and about 0.5%, between about 0.1% and about 0.4%, or about 0.3% and can provide eluted drug(s) in therapeutically useful amounts for periods ranging e.g., for at least 24 hours and preferably at least 70, 100, 250, 500 or even 750 hours or more.

As previously indicated, the dimensions of the drug-eluting device can vary considerably. Thus, the surface dimensions of the device can be such as to exceed, match or be less than that of the surface dimensions of the anterior spinal plate to which it is affixed. By way of illustration, in the case of an anterior cervical plate having an average major surface dimension (e.g., length) of 25 mm and a minor surface dimension (e.g., width) of 12 mm, the drug-eluting device to be affixed thereto can possess a length of from 5 to 27 mm and a width of from 2 to 14 mm.

The thickness of the drug-eluting device can influence the rate and/or amount of drug released from the device and can vary considerably depending on the drug release profile desired. In one embodiment, the thickness of the drug-eluting matrix component of the drug-eluting device can range, e.g., from 0.1 mm to 7 mm, 0.2 mm to 4 mm, 0.1 mm to 2.5 mm, from 0.1 mm to 2 mm, from 0.1 mm to 1 mm, or from 0.3 mm to 1 mm.

The drug(s) selected for incorporation in the drug-eluting device can be in their essentially pure and/or concentrated form, e.g., a powder, a semi-solid or a liquid of widely varying appearance. The physical properties and characteristic elution rates from a given drug-eluting matrix can be determined by a person of ordinary skill in the art, including when the drug is encased in a dissolvable solid bead or liposome for delayed release. When desired, a drug can be incorporated in the drug-eluting matrix in both an encapsulated form and a free form via suitable carrier liquids, e.g., solvents, in particular, water, organic solvent(s) or aqueous mixtures of organic solvent(s). In addition, the drug-eluting matrix may optionally contain one or more non-drug materials, e.g., one or more of those previously recited, dissolved, suspended or dispersed therein. It will, of course, be appreciated that when the physical form of the pure and/or concentrated drug is that of a solid or semi-solid, it may be beneficial if at least some portion of the carrier with the drug(s) dissolved, suspended or dispersed therein is retained in the polymer matrix for subsequent delivery of such drug(s) to the surrounding region of tissue.

The drug, or drugs, incorporated in the drug-eluting matrix of the drug-eluting device herein include, inter alia, anti-infective agents such as antibiotics, antiseptics, antiviral agents and anti-fungal agents, anti-inflammatory agents, local anesthetics and/or any of numerous other classes of therapeutic agents.

Any antibiotic suitable for use in a human may be used in accordance with various embodiments of the invention. As used herein, "antibiotic" means an antibacterial agent. The antibacterial agent may have bateriostatic and/or bacteriocidal activities. Nonlimiting examples of classes of antibiotics that may be used include tetracyclines (e.g. minocycline), rifamycins (e.g. rifampin), lincosamides (e.g. clindamycin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, clindamycin, erythromycin, nafcillin, cefazolin, imipenem, aztreonam, gentamicin, sulfamethoxazole, vancomycin, ciprofloxacin, trimethoprim, metronidazole, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in U.S. Pat. No. 4,642,104, the entire contents of which are incorporated by reference herein, may also be used. One of ordinary skill in the art will recognize still other antibiotics that may be used.

In general, it is desirable that the selected antibiotic(s) kill or inhibit the growth of one or more bacteria that are associated with infection following surgical implantation of a medical device. Such bacteria are recognized by those of ordinary skill in the art and include *Staphylococcus aureus, Staphylococcus epidermis, Staphylococcus capitis, Escherichia coli*, and *Acinetobacter baummanii*. Preferably, the antibiotic(s) selected are effective against strains of bacteria that are resistant to one or more antibiotic.

To enhance the likelihood that bacteria will be killed or inhibited, it may be desirable to combine two or more antibiotics. It may also be desirable to combine one or more antibiotics with one or more antiseptics. It will be recognized by one of ordinary skill in the art that using two or more antimicrobial agents having different mechanisms of action and/or different spectrums of action may be most effective in achieving the desired effect. In one embodiment, a combination of rifampin and minocycline is used, wherein the minocycline is present at weight percent of between about 0.02% and about 0.8%, between about 0.09% and about 0.3%, between about 0.1% and about 0.2% or about 0.2% and the rifampin is present at weight percent of between about 0.03% and about 1.0%, between about 0.09% and about 0.5%, between about 0.1% and about 0.4%, or about 0.3%. In another embodiment, a combination of rifampin and clindamycin is present at weight percent of between about 0.02% and about 0.3%, between about 0.09% and about 0.3%, between about 0.1% and about 0.2% or about 0.15% and rifampin is present at weight percent of between about 0.01% and about 0.1%, between about 0.04% and about 0.07%, between about 0.05% and about 0.06%, or about 0.054%.

Any antiseptic suitable for use in a human may be used in accordance with various embodiments of the invention. As used herein, the term "antiseptic" means an agent capable of killing or inhibiting the growth of one or more of bacteria, fungi, or viruses. Antiseptic includes disinfectants. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver-containing compounds (silver sulfadiazine, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

It is desirable that the selected antimicrobial(s) kill or inhibit the growth of one or more microbial species that are associated with infection following surgical implantation of a medical device. Such microbes are recognized by those of ordinary skill in the art and include *Staphylococcus aureus, Staphylococcus epidermis, Escherichia coli, Pseudomonas aeruginosa,* and *Candida.*

To enhance the likelihood that microbes will be killed or inhibited, it may be desirable to combine two or more antimicrobial agents. It may also be desirable to combine one or more antiseptics with one or more antimicrobial agents. It will be recognized by one of ordinary skill in the art that antimicrobial agents having different mechanisms of action and/or different spectrums of action may be most effective in achieving the desired effect of inhibiting a broad spectrum of potentially infectious microbes and/or drug resistant microbes. In a exemplary embodiment, a combination of chlorohexidine and silver sulfadiazine is used. In another exemplary embodiment, a combination of rifampin and clindamycin is used.

Any antiviral agent suitable for use in a human may be used in accordance with various embodiments of the invention. Nonlimiting examples of antiviral agents include acyclovir and acyclovir prodrugs, famcyclovir, zidovudine, didanosine, stavudine, lamivudine, zalcitabine, saquinavir, indinavir, ritonavir, n-docosanol, tromantadine and idoxuridine. One of ordinary skill in the art will recognize other antiviral agents that may be employed in accordance with this invention.

To enhance the likelihood that viruses will be killed or inhibited, it may be desirable to combine two or more antiviral agents. It may also be desirable to combine one or more antiseptics with one or more antiviral agent.

Any anti-fungal agent suitable for use in a human may be used in accordance with various embodiments of the invention. Nonlimiting examples of anti-fungal agents include amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione. One of ordinary skill in the art will recognize other anti-fungal agents that may be employed in accordance with this disclosure.

To enhance the likelihood that viruses will be killed or inhibited, it may be desirable to combine two or more anti-fungal agents. For example, use of a protein synthesis inhibiting agent, such as minocycline, clindamycin, tetracycline, or doxycycline may be used in combination a DNA dependent RNA polymerase inhibitor such as rifampin or rifapentine. It may also be desirable to combine one or more antiseptics with one or more anti-fungal agent.

Any anti-inflammatory agent suitable for use in a human may be used in accordance with various embodiments of the invention. Non-limiting examples of anti-inflammatory agents include steroids, such as cortisone, hydrocortisone, prednisone, dexamethasone, methyl-prednisilone, an, derivatives thereof; and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

Non-limiting examples of other pharmacological agents that may be used include: beta-radiation emitting isotopes, beclomethasone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin; antineoplastic/antiangiogenic agents, such as antimetabolite agents, alkylating agents, cytotoxic antibiotics, vinca alkaloids, mitosis inhibitors, platinum compounds, tissue growth factor inhibitors, cisplatin and etoposide; immunosuppressant agents, such as cyclosporine A, mycophenolic acid, tacrolimus, rapamycin, rapamycin analogue (ABT-578) produced by Abbott Laboratories, azathioprine, recombinant or monoclonal antibodies to interleukins, T-cells, B-cells and/or their receptors; anticoagulents, such as heparin and chondroiten sulfate; platelet inhibitors such as ticlopidine; vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol; thrombolytic agents, such as stretokinase, urokinase and tissue plasminogin activators; analgesics and antipyretics, such as the opioid analgesics such as buprenorphine, dextromoramide, dextropropoxyphene, fentanyl, alfentanil, sufentanil, hydromorphone, methadone, morphine, oxycodone, papavereturn, pentazocine, pethidine, phenopefidine, codeine dihydrocodeine; acetylsalicylic acid (aspirin), paracetamol, and phenazone; and, antiproliferative agents such as QP-2 (taxol), paclitaxel, rapamycin, tacrolimus, everolimus, actinomycin, methotrexate, angiopeptin, vincristine, mitocycin, statins, C-MYC antisense, sirolimus, restenASE, 2-chloro-deoxyadenosine, PCNA (proliferating cell nuclear antigent) ribozyme, batimastat, prolyl hydroxylase inhibitors, halofuginone, C-proteinase inhibitors, and probucol; and combinations and/or derivatives thereof.

The drug-eluting device, drug-eluting matrix and/or affixation feature can optionally be made of or coated with at least one substance that facilitates non-irritating motion of the device or affixation feature across adjacent tissue and/or at least one anti-adhesion substance.

Suitable friction-reducing materials comprise silicone, hydrogel, xerogel, polyethylene, lotions, lubricants, oils, greases, fluoro-polymer, hydrophilic agents, and combinations thereof. The substance can be present in the drug-eluting matrix and/or affixation feature or in a separate coating(s) in an amount to achieve the desired level of non-irritation motion of the device and/or affixation feature across adjacent tissue.

Suitable anti-adhesion agents refer to chemical or physical agents that form a barrier on a surface the device and through the absence of cohesive strength and/or weak boundary layers, reduces or prevents adhesion of that surface of the device to a material such as, but not limited to, another portion of the device or an uncoated portion of the device. Examples of suitable physical anti-adhesion agents include, without limitation, solid glass spheres, glass bubbles, other mineral, or polymeric particles. Suitable anti-adhesion agents include any surface active compositions which reduces the surface tack of the device. These agents may be known polymeric anti-adhesion agents such as silicones and fluorine containing polymers, for example. These agents may also consist of known biosorbable and biodegradable compositions which act to reduce the surface adhesive properties. These agents may further include intermediate molecular weight compounds such as oligomers of polyethers and alkanes, or biological oils such as fatty esters, to name a few. These agents may also be low molecular weight surface active compounds such as low molecular weight silicones, fluorinated materials, or biological compounds such as sugars.

Chemical anti-adhesion agents may further include various surfactant compositions which may be nonionic or ionic in composition. Nonionic surfactants are defined as those agents which are amphiphilic in nature but do not readily ionize in aqueous solution. Nonionic surfactants may include, for example $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl mondocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof, sucrose fatty acid esters such as sucrose distearate and sucrose palmitate; sorbitan fatty acid esters such as sorbitan monostearate, sorbitan monopalmitate and sorbitan tristerate; $C_{16}$-$C_{18}$ fatty alcohols such as cetyl alcohol, myristyl alcohol, stearyl alcohol, and cetostearyl alcohol, esters of fatty alcohols or fatty acids such as cetyl palmitate and cetearyl palmitate; anhydrides of fatty acids such as stearic anhydride. Nonionic surfactants may further include various metallic salts, such as calcium stearate, magnesium stearate, and zinc stearate, to name a few. Nonionic surfactants may also include organo-onium compounds. Ionic surfactants are defined as those agents which are polar in nature and readily ionize in solution. Ionic surfactants would generally include organic compounds containing salts of strong acid and bases. Examples of ionic surfactants would include, for example, lauryl sulfates such as ammonium lauryl sulfate. Ionic surfactants may further include certain biological lipids, such as phosphatidyl coline. The chemical or physical anti-adhesion agent can be present in the drug-eluting matrix and/or affixation feature or in a separate coating(s) in an amount to achieve the desired level of anti-adhesion.

An adhesive-backed sheet made of an silicone elastomer and silicone adhesive with a length of 20 mm, a width of 10 mm, and a thickness of less than 2 mm may be used as a drug-eluting device for an anterior cervical plate. The sheet may contain rifampin and clindamycin and/or minocycline at the weight percentages set out herein. The drugs can be incorporated into the silicone before, during or after the curing of the silicone. In one example, the drugs can be mixed into a room temperature vulcanized (RTV) silicone elastomer prior to molding or casting. Alternately, the drugs may be incorporated into the silicone elastomer via a solvent-swelling method. The silicone matrix loaded with the antimicrobial drugs is sterilized by heating using steam, e.g., autoclaving, and supplied to the operating room in sterile packaging. The sheet is affixed to the anterior cervical plate before, during or after implantation of the plate in order to provide the implanted tissue areas with locally released antibiotics.

A drug-eluting device may be manufactured by dissolving one or more drugs, for example, rifampin and clindamycin, in a solvent that swells the matrix, such as silicone, for example, using methylene chloride, xylene, or chloroform as the solvent and swelling agent for a silicone matrix. The concentration of each drug can be varied between 0.1 to 0.8 grams per deciliter. For example, for a silicone matrix 0.35 g/dL of Clindamycin in and 0.27 g/dL of rifampin dissolved in chloroform may be used. After about 30 min to 1 hr, the solvent may be removed and optionally purged with nitrogen for about 30 min, the drug-eluting device may then be dried, for example, alternate drying under vacuum and purging with nitrogen may be used to drive off the solvent. The drug-loaded elution devices may then be packaged for sterilization by steam. HPLC analysis may be used to show the achieved weight percent loading of Rifampin and Clindamycin.

Methods of affixing the drug-eluting device of the foregoing example are illustrated in FIGS. 1-6.

As shown in FIG. 1, an anterior spinal plate 10 of known design measuring an average of 30 mm in length, 12 mm in width and 2.5 mm in thickness and fabricated from any suitable material, e.g., metal, bioresorbable polymer, non-bioresorbable polymer, ceramic, inorganic/organic composite, etc., features openings 11 for receiving each of screws 12 for securing plate 10 to spinal bone at a desired location. As anterior spinal plate 10 is being screwed to the spinal bone, rectangular-shaped drug-eluting device 20 fabricated as described above is simultaneously affixed to the surface of the plate by the same screws 12.

Figure 2:
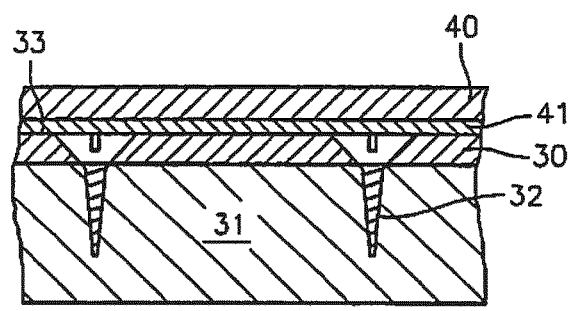
FIG. 2 is a side elevation view of one embodiment of anterior spinal plate of this invention secured to spinal bone, the plate having the drug-eluting device affixed thereto via biocompatible adhesive.

In the embodiment of installed anterior spinal plate shown in side elevation view in FIG. 2, anterior spinal plate 30 secured to spinal bone surface 31 via screws 32 possesses drug-eluting device 40 affixed to surface 33 of device 40 by a layer of biocompatible adhesive 41 previously applied to a surface of device 40. Biocompatible adhesives include cyanoacrylate, epoxy, silicone, acrylics, polyvinyl alcohol, polyurethane, albumin, collagen, etc. and mixtures thereof.

Figure 3:
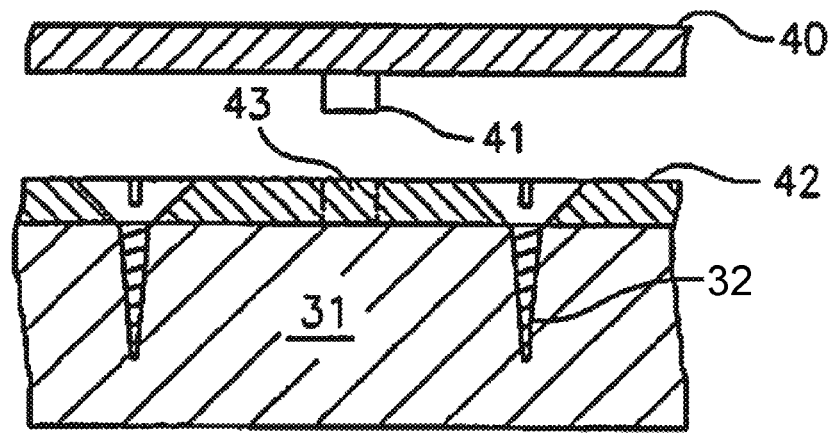
FIG. 3 is a side elevation view of one embodiment of anterior plate and the snap fit/pressure fit.

In the embodiment of installed anterior spinal plate shown in side elevation view FIG. 3, anterior spinal plate 42 secured to spinal bone surface 31 via screws 32 further comprises a cavity 43. FIG. 3 also shows a drug eluting matrix 40 having an extension 41 configured to pressure fit/friction fit into the cavity 43 on the secured anterior plate.

Figure 4:
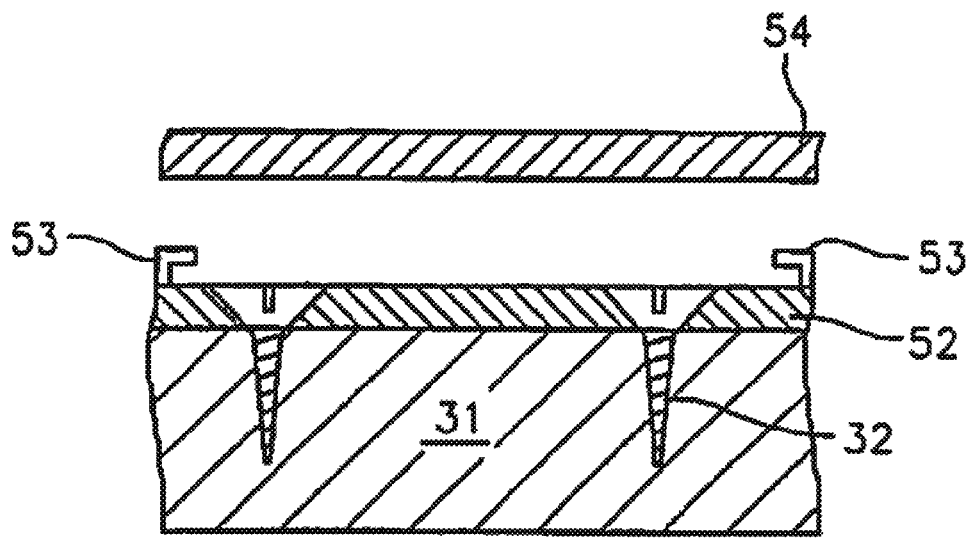
FIG. 4 is a side elevation view of one embodiment of anterior plate having locking elements configured to engage the drug-eluting matrix.

FIG. 4 shows an alternative embodiment of anterior plate 52 secured to spinal bone surface 31 via screw 32 further comprising locking elements such as flanges 53 positioned on the edges of the anterior plate 52. In this embodiment, the drug-eluting matrix 54 is held in place by flange 53 (or multiple flanges). The flange 53 can be configured so as to lock into or pressure fitted with the drug-eluting matrix 54.

Figure 6:
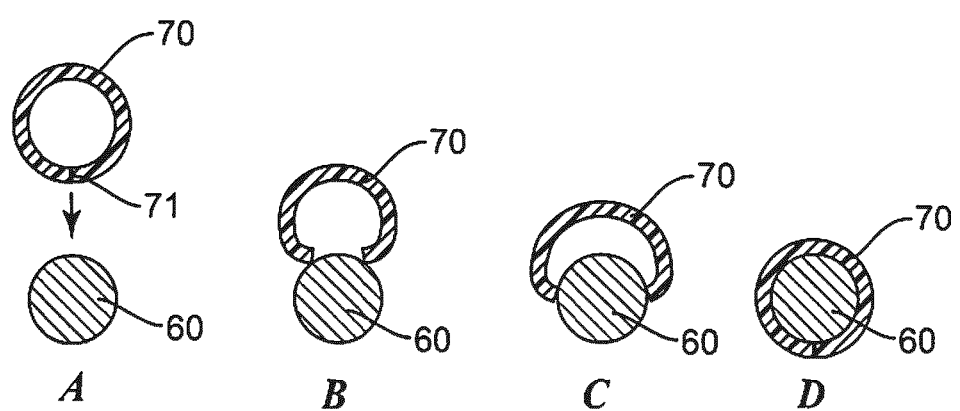
FIG. 6 is a perspective view of the rod component of a spinal fixation system and a performed drug-eluting sleeve in accordance with this invention being affixed to the rod with the affixation of the sleeve to the rod being illustrated in the cross sectional views A-D.

One method of affixation of these and similar-type cylindrical sleeves to the spinal rod is illustrated in FIG. 5. Preformed drug-eluting cylindrical sleeve 70 made of a silicone elastomer and possessing lengthwise slit 71 is press-fitted to spinal rod 60. 5A shows the cross-sectional line. FIG. 6 shows sequence A-D illustrating the deformation of the sleeve under continuously applied pressure until it snaps fully in place (stage D).

Other configurations are also possible, for example, configurations that use the above-discussed structural and adhesive components to attach the drug-eluting matrix to the anterior spinal plate of the invention fall within the invention.

The following examples are illustrative of the manufacture of the drug-eluting device of the anterior spinal plate of the invention.

EXAMPLES

A cylindrical sleeve made of silicone elastomer and having an average wall thickness of 0.4 mm to 2.5 mm was used as a drug-eluting device for a steel spinal rod component of a known or conventional spinal fixation system. The sleeve contains minocycline at a loading of about 2.0 µg/mg and rifampin at a loading of about 3.0 ug/mg (0.2 wt % minocycline and 0.3 wt % rifampin). See FIG. 5 for a perspective view of a cylindrical sleeve used as a drug-eluting device for a spinal rod component.

A substantially identical cylindrical sleeve of silicone elastomer contains clindamycin at 0.15 weight percent and rifampin at 0.054 weight percent.

Methods and Procedures

Custom In-Life Studies: Device Infection Model Development

A clinical problem when using implants is that 3-5% of implants develop infection. Infections often involve formation of microbial biofilms around the implant which are very resistant to standard antibiotic therapies resulting in high morbidity and mortality of patients. Treatment often requires removal of the infected implant, debridement, and replacing with new implant(s) at a very high cost. Further, reimbursement for treating hospital-acquired infections is being limited.

Spinal Device Infection Animal Model: Specific Considerations

Figure 9A:
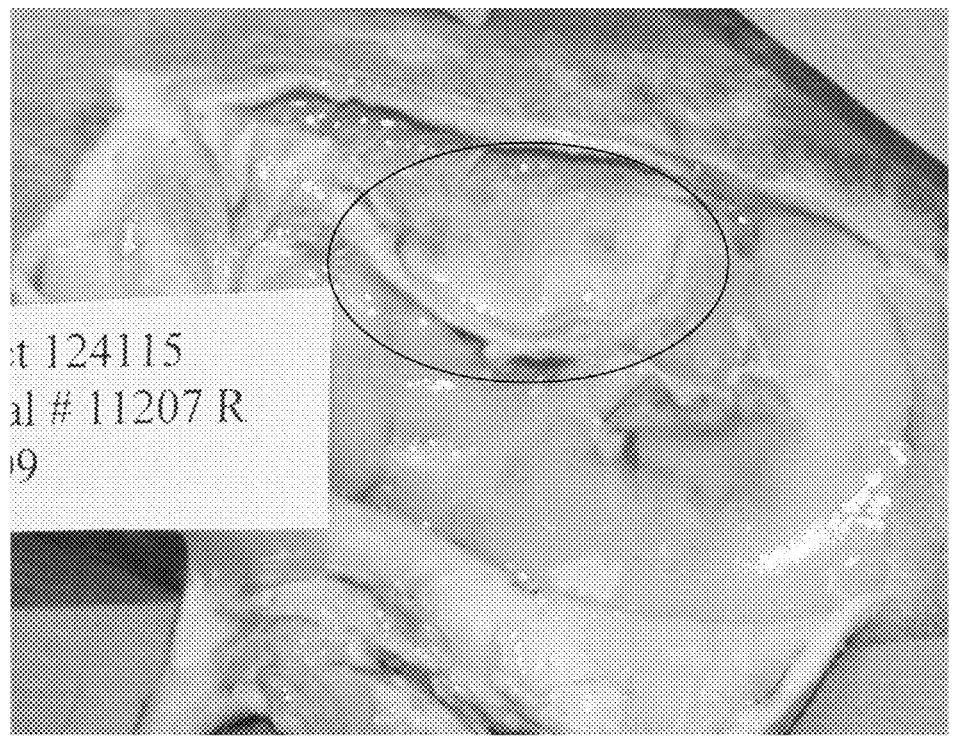
Figure 9B:
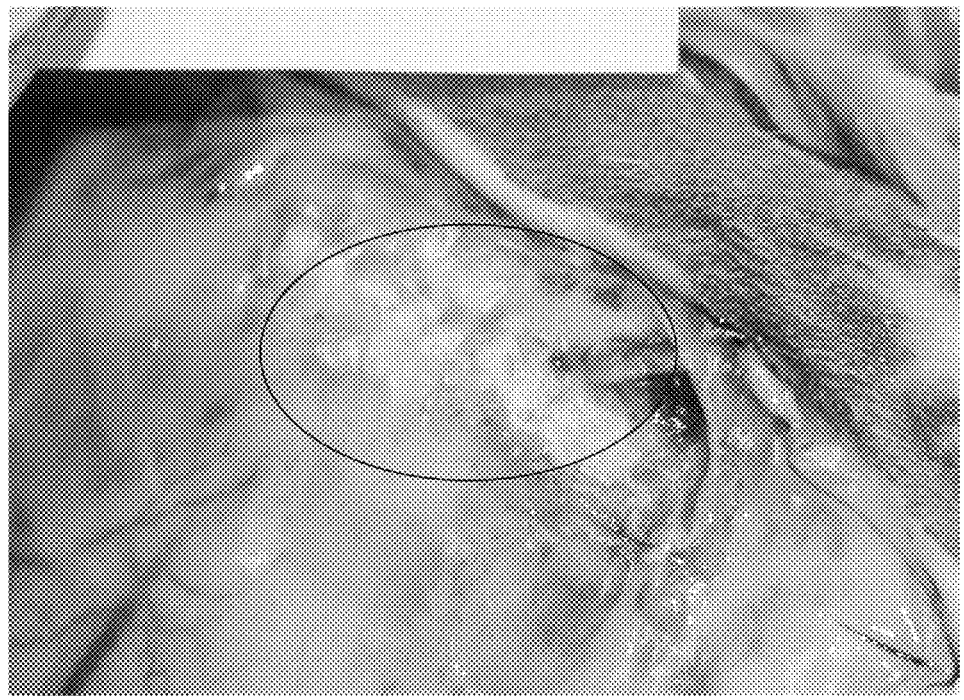
FIG. 9b shows a clean rabbit suture line of a nanosilver coated implant also 7 days after being implanted, non-infected control.
Figure 10:
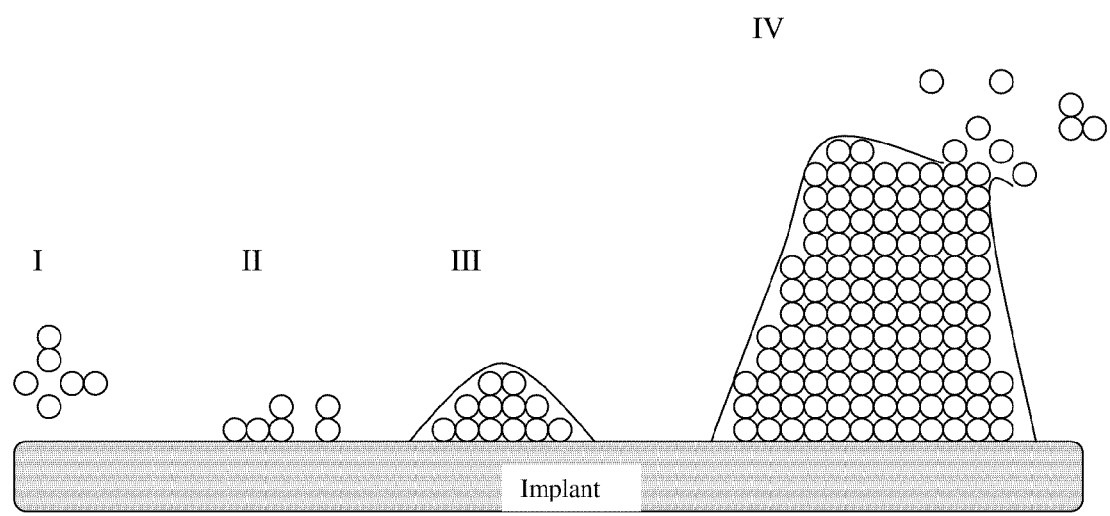
FIG. 10 illustrates biofilm formation with initial attachment of the microbes to the surface of the implant (I), expansion of the population (II), maturation of the population within the biofilm (III), and finally disruption of the biofim (IV) and liberation of the microbes into the surrounding tissue where they can again recolonize the implant or migrate elsewhere in the subject (sonication was used to disrupt the biofilm prior to assaying for the presence of microbes)
Figure 11:
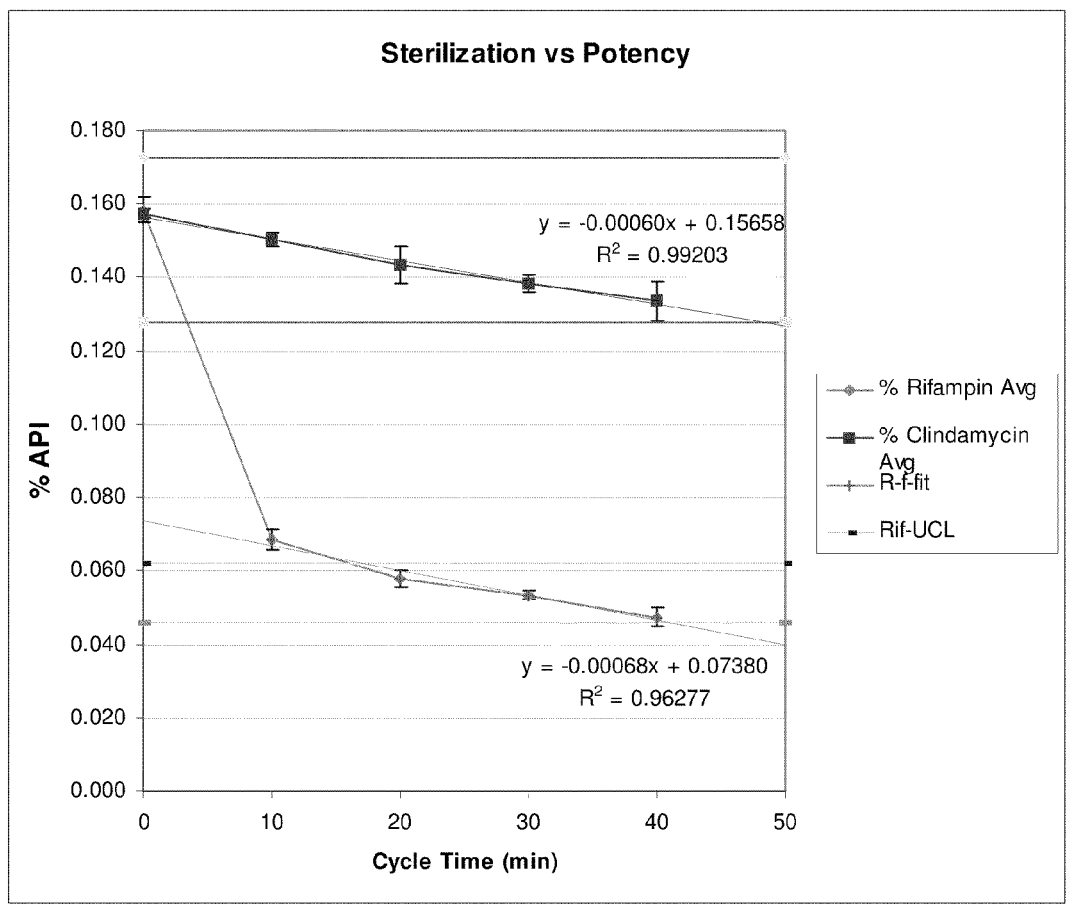
FIG. 11 illustrates the effect of sterilization on the final drug concentration, showing the degradation rate versus autoclave time, for example, with a starting concentration of about 0.0738 wt % rifampin in the silicone and running the autoclave about 30 minutes will result in a final concentration of about 0.054 wt % rifampin in the silicone sleeve.

Considerations in the design of spinal implant(s) in the anti-microbial tests include: studying designs which are specific to the anticipated clinical situation involve such choices as the spinal implant site location, the combination of a particular screw and rod to mimic the geometry as it will exist in human patients, using clinically relevant microbes such as *S. aureus*, using reproducible and quantifiable endpoints such as by using sonications of the explanted screw/rod to recover adherent bacterial ("biofilm", See FIG. 9), creating infection with dose(s) high enough to create consistent infection without mortality, but low enough to be amenable to treatment in dosing studies and other consideration in the study design that will effectively show a reduction of infection.

Device Infection Studies—Microbial Pathogens

Microorganism strains used in past studies include *Staphylococcus aureus* (MSSA, MRSA), *Staphylococcus epidermidis*, *Staphylococcus capitis*, *Escherichia coli*, *Acinetobacter baummanii*, *Pseudomonas aeruginosa* and *P. Acnes*. Each strain can be obtained from ATCC (American Type Culture Collection) or characterized clinical isolate from Sponsor. Each new organism requires In vitro characterization to determine the growth curve and in vivo dosing studies are required to determine a dose that creates consistent infection without mortality.

Dosing Study of In Vivo Spinal Screw Infection

In the study design (final of 3 dosing studies) there are three dosage groups ($1\times10^3$, $1\times10^2$, $2\times10^1$ CFU) including 2-3 animals per group with testing performed on bilateral sites. The test implant was an uncoated spinal screw and rod which were implanted for 7 days. The explant measurements include photograph documentation of the implant site, recordation of gross observations, radiographs (post-surgical and termination to confirm test implant placement), hematology and sonication/vortex of explanted screw/rod set to assess bacteria on the implant.

TABLE 1

Dosing Study: Device Sonication Results

| Group (Dose) | Animal # | Side | Sonicant 1 | | | | | Sonicant 2 | | | | | Swab | Blood | Isolate Identification | |
|---|---|---|---|---|---|---|---|---|---|---|---|---|---|---|---|---|
| | | | U | $10^{-1}$ | $10^{-2}$ | $10^{-3}$ | Cfu/mL | U | $10^{-1}$ | $10^{-2}$ | $10^{-3}$ | Cf/mL | | | Gram Stain | API ID |
| 1000 CFU per site | 10837 | Right | TNC | TNC | TNC | 134 | 6.70E+05 | TNC | TNC | 82 | 4 | 4.10E+04 | + | − | GPC | SA |
| | | Left | TNC | TNC | TNC | 49 | 2.45E+05 | TNC | TNC | 57 | 5 | 2.85E+04 | + | − | GPC | SA |
| | 10839 | Right | TNC | TNC | TNC | 80 | 4.00E+05 | TNC | TNC | 112 | 15 | 5.60E+04 | + | − | GPC | SA |
| | | Left | TNC | TNC | TNC | 212 | 1.06E+06 | TNC | TNC | TNC | 21 | 1.05E+05 | + | − | GPC | SA |
| | NA | | | | | | | | | | | | | | | |
| 100 CFU per site | 10840 | Right | TNC | TNC | TNC | 122 | 6.10E+05 | TNC | TNC | TNC | 37 | 1.85E+05 | + | − | GPC | SA |
| | | Left | TNC | TNC | TNC | TNC | TNC | TNC | TNC | TNC | 115 | 5.75E+05 | + | − | GPC | SA |
| | 10844 | Right | TNC | TNC | TNC | 160 | 8.00E+05 | TNC | TNC | TNC | 52 | 2.60E+05 | + | − | GPC | SA |
| | | Left | TNC | TNC | TNC | 74 | 3.70E+05 | TNC | TNC | 110 | 12 | 5.50E+04 | + | − | GPC | SA |
| | 10843 | Right | TNC | TNC | TNC | 20 | 1.00E+05 | TNC | TNC | 68 | 20 | 3.40E+04 | + | − | GPC | SA |
| | | Left | TNC | TNC | 94 | 8 | 4.70E+04 | TNC | TNC | 76 | 6 | 3.80E+05 | + | − | GPC | SA |

TABLE 1-continued

Dosing Study: Device Sonication Results

| Group (Dose) | Animal # | Side | Sonicant 1 U | $10^{-1}$ | $10^{-2}$ | $10^{-3}$ | Cfu/mL | Sonicant 2 U | $10^{-1}$ | $10^{-2}$ | $10^{-3}$ | Cf/mL | Swab | Blood | Isolate Identification Gram Stain | API ID |
|---|---|---|---|---|---|---|---|---|---|---|---|---|---|---|---|---|
| 20 CFU per site | 10841 | Right | TNC | TNC | TNC | 106 | 5.30E+05 | TNC | TNC | 88 | 16 | 4.40E+04 | + | − | GPC | SA |
| | | Left | TNC | TNC | TNC | TNC | TNC | TNC | TNC | 198 | 28 | 9.90E+04 | + | − | GPC | SA |
| | 10842 | Right | TNC | TNC | TNC | 136 | 6.80E+05 | TNC | TNC | 120 | 18 | 6.00E+04 | + | − | GPC | SA |
| | | Left | 16 | 1 | 0 | 0 | 8.00E+02 | 0 | 1 | 0 | 0 | 5.00E+01 | + | − | GPC | SA |
| | 10838 | Right | 0 | 0 | 0 | 0 | 0 | 0 | 0 | 0 | 0 | 0 | + | − | GPC | SA |
| | | Left | 0 | 0 | 0 | 0 | 0 | 0 | 0 | 0 | 0 | 0 | + | − | GPC | SA |

TABLE 2

Dosing Study: Summary Table

| Group (Target Dose) | Actual Dose | 1st Sonication Recovery (ave. CFU/mL) | 2nd Sonication Recovery (ave. CFU/mL) | Swab (+/−) |
|---|---|---|---|---|
| High Dose ($1 \times 10^3$) | $0.4$–$0.8 \times 10^3$ | $5.9 \times 10^5$ (4/4 positive) | $5.8 \times 10^4$ (4/4 positive) | +(4/4) |
| Midde Dose ($1 \times 10^2$) | $0.9$–$1.2 \times 10^2$ | $5.2 \times 10^5$ (6/6 positive) | $1.9 \times 10^5$ (6/6 positive) | +(6/6) |
| Low Dose ($2 \times 10^1$) | $0.8$–$0.9 \times 10^1$ | $5.4 \times 10^5$ (5/6 positive) | $5.0 \times 10^4$ (5/6 positive) | +(6/6) | silver coating A (the low coating) and coated with silver coating B (the high coating). The *Staphylococcus aureus* dose was $1 \times 10^2$ CFU total per site. There were 3 animals per group with studies on bilateral sites. The test implant was a spinal screw with an uncoated (control) or coated rod which was implanted into the rabbit model for 7 days (see FIGS. 8a and 8b). Measurements of the explanted device included photograph documentation of the implant site (see FIGS. 9a and 9b), recordation of gross observations, radiographs (post-surgical and at termination to confirm proper test implant placement, see FIG. 7b), hematology and sonication/vortexing (of two animals) of explanted screw/rod sets to assess bacteria on device.

TABLE 3

Sonication Results: Efficacy Study #1 - NanoSilver

| Group | Animal # | Side | Sonicant 1 U | $10^{-1}$ | $10^{-2}$ | $10^{-3}$ | CFU/mL | Sonicant 2 U | $10^{-1}$ | $10^{-2}$ | $10^{-3}$ | CFU/mL | Swab | Blood | Isolate Identification Gram Stain | API ID |
|---|---|---|---|---|---|---|---|---|---|---|---|---|---|---|---|---|
| Control | 11206 | Right | TNC | TNC | TNC | 154 | 7.70E+05 | TNC | TNC | 116 | 11 | 5.80E+04 | + | − | GNC | SA |
| | | Left | TNC | TNC | TNC | 106 | 5.30E+05 | TNC | TNC | 178 | 19 | 8.90E+04 | + | − | GPC | UP |
| | 11207 | Right | TNC | TNC | TNC | 180 | 9.00E+05 | TNC | TNC | 83 | 14 | 4.15E+04 | + | − | GNC | SA |
| | | Left | TNC | TNC | 243 | 28 | 1.22E+05 | TNC | TNC | 64 | 7 | 3.20E+04 | + | − | GPC | SA |
| | 11208 | Right | TNC | TNC | TNC | 160 | 8.00E+05 | TNC | TNC | 260 | 23 | 1.30E+05 | + | − | GPC | SA |
| | | Left | TNC | TNC | TNC | 167 | 8.35E+05 | TNC | TNC | 220 | 15 | 1.10E+05 | + | − | GVC | SA |
| Coating A | 11209 | Right | TNC | TNC | TNC | 143 | 7.15E+05 | TNC | TNC | TNC | 75 | 3.75E+05 | + | − | GVC | SA |
| | | Left | TNC | TNC | 165 | 28 | 8.25E+05 | TNC | TNC | 45 | 5 | 2.25E+04 | + | − | GPC | SA |
| | 11210 | Right | TNC | TNC | TNC | 292 | 1.46E+06 | TNC | TNC | TNC | 89 | 4.45E+05 | + | − | GPC | SA |
| | | Left | TNC | TNC | TNC | 167 | 7.65E+05 | TNC | TNC | 169 | 10 | 8.45E+04 | + | − | GPC | SA |
| | 11211 | Right | TNC | TNC | TNC | 106 | 5.30E+05 | TNC | TNC | 197 | 12 | 9.85E+04 | + | − | GPC | SA |
| | | Left | TNC | TNC | TNC | TNC | TNC | TNC | TNC | TNC | 96 | 4.80E+05 | + | − | GPC | SA |
| Coating B | 11200 | Right | TNC | TNC | TNC | 111 | 5.55E+05 | TNC | TNC | 265 | 29 | 1.33E+05 | + | − | GNC | SA |
| | | Left | TNC | TNC | TNC | 133 | 6.65E+05 | TNC | TNC | TNC | 42 | 2.10E+05 | + | − | GPC | SA |
| | 11201 | Right | TNC | TNC | TNC | 240 | 1.20E+06 | TNC | TNC | TNC | 44 | 2.20E+05 | + | − | GVC | SA |
| | | Left | TNC | TNC | TNC | 162 | 8.10E+05 | TNC | TNC | TNC | 49 | 2.45E+05 | + | − | GVC | SA |
| | 11202 | Right | TNC | TNC | TNC | 39 | 1.95E+05 | TNC | TNC | 242 | 26 | 1.21E+05 | + | − | GVC | SA |
| | | Left | TNC | TNC | TNC | 72 | 3.60E+05 | TNC | TNC | 236 | 22 | 1.18E+05 | + | − | GPC | SA |

Three rabbit implant studies were conducted comparing microbial growth on implants coated with nanosilver and implants coated with specific combinations of antibiotics. Below are tables that outline 3 study groups, namely nanoSilver (Efficacy Study #1), Minocycline/Rifampin and Clindamycin/Rifampin (M/R coating and C/R coating-Efficacy Study #2).

Efficacy Study #1—Nanosilver Coating

Study Design (efficacy study, silver coatings): Three study groups include implants which are uncoated, coated with

TABLE 4

Efficacy Study #1 (Ag): Summary Table

| Group (Target Dose) | Actual Dose (Target Dose = $1 \times 10^2$ Total CFU) | 1st Sonication Recovery (ave. CFU/mL) | 2nd Sonication Recovery (ave. CFU/mL) | Swab (+/−) |
|---|---|---|---|---|
| Control (No Coating) | $0.9 \times 10^2$ | $6.5 \times 10^5$ (6/6 positive) | $7.7 \times 10^4$ (6/6 positive) | +(6/6) |
| Low Coating | $0.9 \times 10^2$ | $9.7 \times 10^5$ (6/6 positive) | $2.8 \times 10^5$ (6/6 positive) | +(6/6) |

TABLE 4-continued

Efficacy Study #1 (Ag): Summary Table

| Group (Target Dose) | Actual Dose (Target Dose = $1 \times 10^2$ Total CFU) | $1^{st}$ Sonication Recovery (ave. CFU/mL) | $2^{nd}$ Sonication Recovery (ave. CFU/mL) | Swab (+/−) |
|---|---|---|---|---|
| High Coating | $0.9 \times 10^2$ | $6.3 \times 10^5$ (5/6 positive) | $1.4 \times 10^5$ (5/6 positive) | +(6/6) |

As can be seen from the Summary Table 4, both the high and low dosage levels of silver were ineffective in reducing the average CFU/ml in $1^{st}$ and $2^{nd}$ Sonication Recovery. Thus, it can be concluded that silver is ineffective in preventing/reducing infection in the pocket around the implant.

Efficacy Study #2—Minocycline/Rifampin and Clindamycin/Rifampin

Study Design (efficacy study, antibiotic coatings): Three study groups include implants which were uncoated, coated with Minocycline/Rifampin (M/R coating) or coated with Clindamycin/Rifampin (C/R coating, see U.S. Pat. No. 4,917,686). The *Staphylococcus aureus* dose was $1 \times 10^2$ CFU total per site. There were three animals per group with studies conducted on bilateral sites. The test implant was a spinal screw with an uncoated (control) rod or a rod coated with a drug-eluting device which was implanted into the rabbit model for a duration of 7 days. The Minocycline/Rifampin coating was made with 2.046 μg/mg of minocycline and 2.977 μg/mg of rifampin imbedded in a 0.015 inch or 0.4 mm thick silicone tube that was 2 cm long that weighed 93.6 mg for total drug on the rod of 191 μg minocycline and 278 μg of rifampin ((0.191 mg minocycline÷93.6 mg of silicone)×100=about 0.2% by weight). The Minocycline/Clindamycin coating was made with 0.15 wt % Clindamycin and 0.054 wt % rifampin imbedded in a silicone tube that weighed 174.2 mg for total drug on the rod of 261 μg clindamycin and 94 μg of rifampin ((0.094 mg lindamycin÷174.2 mg of silicone)×100=about 0.054% by weight).

Figure 7A:
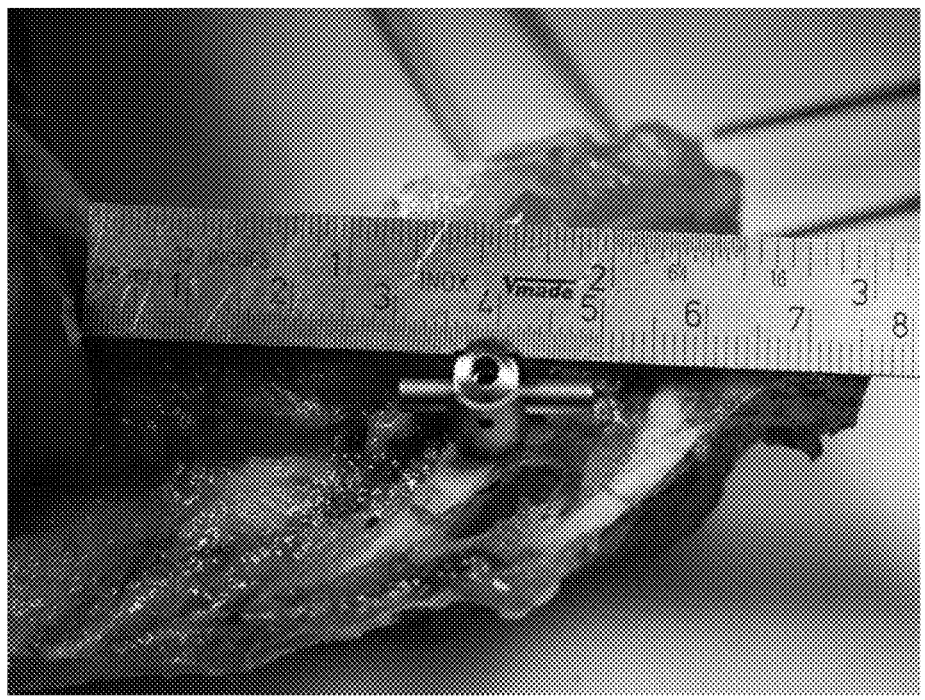
FIGS. 7a and 7b are surgical pictures of an implant positioned in a Rabbit Model used to test the efficiency of nanosilver vs. particular antibiotic combinations provided in the drug-eluting device of the implants.
Figure 7B:
Figure 8A:
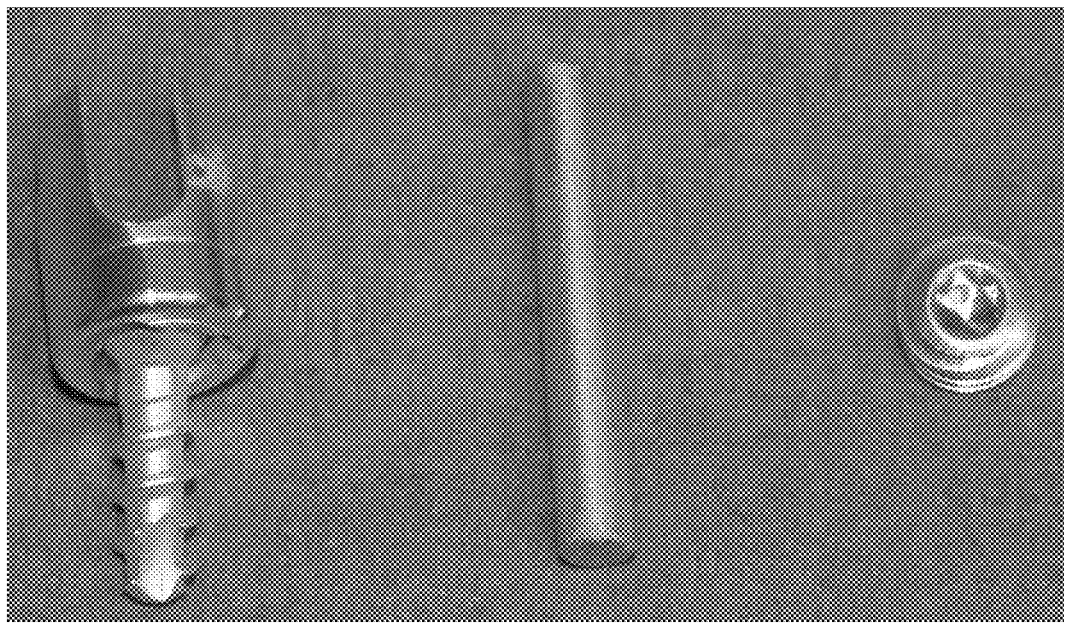
FIGS. 8a and 8b are surgical pictures of the implants coated with nanosilver before implantation and explants after 7 days.
Figure 8B:

The explant measurements include photograph documentation of the implant site (See FIGS. 9a and 9b), recordation of gross observations, radiographs (post-surgical and termination to confirm test implant placement, see FIG. 7b), hematology and sonication/vortex (of three animals) of explanted screw/rod set to assess bacteria on device.

TABLE 5

Sonication Results: Efficacy Study #2

| Group | Animal # | Side | Sonicant 1 U | $10^{-1}$ | $10^{-2}$ | $10^{-3}$ | CFU/mL | Sonicant 2 U | $10^{-1}$ | $10^{-2}$ | $10^{-3}$ | CFU/mL | Swab | Blood | Gram Stain | API ID |
|---|---|---|---|---|---|---|---|---|---|---|---|---|---|---|---|---|
| Control (No Tx) | 11727 | Right | TNC | TNC | TNC | 118 | 5.90E+05 | TNC | TNC | 142 | 17 | 7.10E+04 | + | − | TBD | TBD |
| | | Left | TNC | TNC | TNC | 239 | 1.20E+06 | TNC | TNC | 215 | 17 | 1.08E+05 | + | − | TBD | TBD |
| | 11728 | Right | TNC | TNC | TNC | 180 | 9.00E+05 | TNC | TNC | 83 | 14 | 4.15E+04 | + | − | TBD | TBD |
| | | Left | TNC | TNC | 243 | 28 | 1.22E+05 | TNC | TNC | 64 | 7 | 3.20E+04 | + | − | TBD | TBD |
| | 11728 Sonicant 3: | Right | | | | | | | | 13 | 1 | 8.80E+03 | NA | NA | NA | NA |
| | | Left | | | | | | | | 31 | 2 | 1.55E+04 | NA | NA | NA | NA |
| M/R Tx | 11721 | Right | 0 | 0 | 0 | 0 | 0 | 0 | 0 | 0 | 0 | 0 | − | − | NA | NA |
| | | Left | 0 | 0 | 0 | 0 | 0 | 0 | 0 | 0 | 0 | 0 | − | − | NA | NA |
| | 11722 | Right | 0 | 0 | 0 | 0 | 0 | 0 | 0 | 0 | 0 | 0 | − | − | NA | NA |
| | | Left | 0 | 0 | 0 | 0 | 0 | 0 | 0 | 0 | 0 | 0 | − | − | NA | NA |
| | 11723 | Right | 0 | 0 | 0 | 0 | 0 | 0 | 0 | 0 | 0 | 0 | − | − | NA | NA |
| | | Left | 0 | 0 | 0 | 0 | 0 | 0 | 0 | 0 | 0 | 0 | − | − | NA | NA |
| C/R Tx | 11724 | Right | 0 | 0 | 0 | 0 | 0 | 0 | 0 | 0 | 0 | 0 | − | − | NA | NA |
| | | Left | 0 | 0 | 0 | 0 | 0 | 0 | 0 | 0 | 0 | 0 | − | − | NA | NA |
| | 11725 | Right | 0 | 0 | 0 | 0 | 0 | 0 | 0 | 0 | 0 | 0 | − | − | NA | NA |
| | | Left | 0 | 0 | 0 | 0 | 0 | 0 | 0 | 0 | 0 | 0 | − | − | NA | NA |
| | 11726 | Right | 0 | 0 | 0 | 0 | 0 | 0 | 0 | 0 | 0 | 0 | − | − | NA | NA |
| | | Left | 0 | 0 | 0 | 0 | 0 | 0 | 0 | 0 | 0 | 0 | − | − | NA | NA |

TABLE 6

Summary Table

| Group | Actual Dose (Target Dose = $1 \times 10^2$ Total CFU) | $1^{st}$ Sonication Recovery (ave. CFU/mL) | 2nd Sonication Recovery (ave. CFU/mL) | 3rd Sonication Recovery (ave. CFU/mL) | Swab (positive/total) |
|---|---|---|---|---|---|
| Control (No Treatment) | $1.0$-$1.3 \times 10^2$ | $5.6 \times 10^5$ (4/4 positive) | $7.2 \times 10^4$ (4/4 positive) | $1.9 \times 10^4$ (4/4 positive) | 4/4 |
| M/R Treatment | $1.0$-$1.3 \times 10^2$ | 0 (0/6 positive) | 0 (0/6 positive) | 0 (0/6 positive) | 0/6 |
| C/R Treatment | $1.0$-$1.3 \times 10^2$ | 0 (0/6 positive) | 0 (0/6 positive) | 0 (0/6 positive) | 0/6 |

In summary, it can be seen from the studies conducted that a consistent *Staphylococcus aureus* infection can be created at the implant site. In efficacy study #1, nanosilver coating was shown to be ineffective at reducing infection in the pocket around the device and on the device in this infection model. Efficacy study #2 shows a device containing clindamycin/rifampin and/or minocycline/rifampin treated silicone sleeves covering the rods to be effective at eliminating infection in the pocket and on the device. Thus, antibiotic infused devices of the present invention are effective in eliminating infection and in particular implants affixed with a device comprising a drug-eluting biocompatible matrix containing clindamycin/rifampin and/or minocycline/rifampin were proven to be effective.

While the invention has been illustrated and described in detail the drawings and foregoing description, the same is considered to be illustrative and not restrictive in character, it is understood that only the preferred embodiments have been shown and described and that all changes and modifications that come within the spirit of the invention are desired to be protected. All patent applications, patents and all documents cited herein are hereby incorporated by reference in their entirety.

What is claimed is:

1. A drug-eluting device comprising:
   an open cell drug-eluting matrix containing at least one elutable drug and at least one anti-adhesion substance that facilitates non-irritating motion of the device across adjacent tissue; and
   an anterior spinal plate comprising at least one affixation feature for providing affixation of the drug-eluting matrix to said anterior spinal plate,
   wherein said drug-eluting matrix is configured to engage a surface of said anterior spinal plate and comprises rifampin and minocycline, wherein the rifampin and minocycline are configured to be eluted from said drug-eluting matrix towards said surface of said anterior spinal plate, and
   wherein said anterior spinal plate and said drug-eluting matrix are provided as two separately sterilized components, said anterior spinal plate being sterilized using an autoclave and said drug-eluting matrix being sterilized using sterilizing radiation or sterilant gas.

2. The drug-eluting device of claim 1, wherein the affixation feature is a cavity and said drug-eluting matrix comprises an extension that is configured to be press fit into said cavity.

3. The drug-eluting device of claim 1, wherein the drug-eluting matrix comprises at least one semi-synthetic or fully synthetic polymer.

4. The drug-eluting device of claim 1, wherein the drug-eluting biocompatible matrix comprises a silicone elastomer.

5. The drug-eluting device of claim 1, wherein the drug-eluting matrix is configured such that the rifampin and the minocycline pass directly to the surface of the anterior spinal plate.

6. The drug-eluting device of claim 1, wherein the drug-eluting matrix is configured to have a gradient such that the drug-eluting matrix has a greater concentration of rifampin and minocycline adjacent a surface of the drug-eluting matrix that engages the surface of the anterior spinal plate.

7. The drug-eluting device of claim 1, wherein the drug-eluting matrix comprises 0.03 wt % of rifampin and 0.09 wt % of minocycline post-sterilization.

8. The drug-eluting device of claim 1, wherein the rifampin is present in an amount of between about 0.05 wt % and about 0.06 wt %.

9. The drug-eluting device of claim 1, wherein the drug-eluting matrix is a planar sheet comprising multiple layers.

10. The drug-eluting device of claim 1, wherein the drug-eluting matrix comprises a first layer including the rifampin and a second layer comprising the minocycline.

11. The drug-eluting device of claim 1, wherein the drug-eluting matrix comprises a plurality of drug-eluting matrices.

12. The drug-eluting device of claim 1, wherein said anterior spinal plate is fabricated from a bioresorbable polymer.

13. The drug-eluting device of claim 1, wherein said open cell drug-eluting matrix comprises polyurethane foam.

14. The drug-eluting device of claim 1, wherein at least one of said rifampin and said minocycline are incorporated into said drug-eluting matrix in both an encapsulated form in which said rifampin and/or said minocycline are encased in a dissolvable bead or liposome and in a free form that comprises a liquid carrier.

15. The drug-eluting device of claim 1, wherein said affixation feature is a cavity that extends through opposite top and bottom surfaces of said anterior spinal plate and said drug-eluting matrix comprises an extension that is configured to be press fit into said cavity, said top and bottom surfaces each being planar and free of any projections extending outwardly therefrom.

16. An implant kit comprising:
   an anterior spinal plate; and,
   at least one preformed drug-eluting device comprising an open cell drug-eluting matrix and at least one anti-adhesion substance, said drug-eluting matrix comprising rifampin and minocycline,
   wherein said anterior spinal plate and said at least one preformed drug-eluting device are provided as two separately sterilized components, said anterior spinal plate being sterilized using an autoclave and said at least one preformed drug-eluting device being sterilized using sterilizing radiation or sterilant gas.

17. The implant kit of claim 16, further comprising a plurality of drug-eluting matrices each comprising rifampin and minocycline, wherein each of said plurality of drug-eluting matrices includes a different amount of rifampin and minocycline and wherein each of said plurality of drug-eluting matrices are sterilized using sterilizing radiation or sterilant gas and are provided separately.

18. A system comprising:
   a spinal rod; and
   a hollow drug-eluting device having a cylindrical shape defining a sleeve configured to have said spinal rod positioned therein, said device comprising an open cell drug-eluting biocompatible matrix containing at least one elutable drug and at least one anti-adhesion substance that facilitates non-irritating motion of the device across adjacent tissue, said device comprising a lengthwise slit extending through an inner surface and an outer surface of said device, said inner surface of said device being configured to engage an outer surface of said spinal rod, said device comprising at least one affixation feature for providing affixation of the device to said spinal rod,
   wherein said spinal rod and said device are provided as two separately sterilized components, said spinal rod being sterilized using an autoclave and said device being sterilized using sterilizing radiation or sterilant gas.

19. The system of claim 18 wherein the affixation feature is press-fit elements(s).

20. The system of claim 18, wherein said spinal rod is cylindrical and is free of any openings extending through said spinal rod.

* * * * *